US007962209B2

(12) United States Patent
Bocek et al.

(10) Patent No.: US 7,962,209 B2
(45) Date of Patent: *Jun. 14, 2011

(54) METHOD AND SYSTEM FOR CHARACTERIZING SUPRAVENTRICULAR RHYTHM DURING CARDIAC PACING

(75) Inventors: Joseph Bocek, Seattle, WA (US); Jaeho Kim, Redmond, WA (US); Anthony Harrington, Woodinville, WA (US); Harley White, Carnation, WA (US); Dave Perschbacher, Coon Rapids, MN (US); Rebecca Davis, Portland, OR (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 369 days.

This patent is subject to a terminal disclaimer.

(21) Appl. No.: 12/283,220

(22) Filed: Sep. 10, 2008

(65) Prior Publication Data

US 2009/0043347 A1 Feb. 12, 2009

Related U.S. Application Data

(60) Continuation of application No. 11/097,458, filed on Apr. 1, 2005, now Pat. No. 7,426,411, which is a division of application No. 10/121,944, filed on Apr. 12, 2002, now Pat. No. 6,889,079.

(51) Int. Cl.
*A61N 1/00* (2006.01)
(52) U.S. Cl. .......................................................... 607/9
(58) Field of Classification Search ............... 607/4–28
See application file for complete search history.

(56) References Cited

U.S. PATENT DOCUMENTS

| | | |
|---|---|---|
| 5,000,189 A | 3/1991 | Throne et al. |
| 5,217,021 A | 6/1993 | Steinhaus et al. |
| 5,447,519 A | 9/1995 | Peterson |
| 5,779,645 A | 7/1998 | Olson et al. |
| 5,817,027 A | 10/1998 | Arand et al. |
| 5,857,977 A | 1/1999 | Caswell et al. |
| 6,035,232 A | 3/2000 | Thong et al. |
| 6,052,620 A | 4/2000 | Gillberg et al. |
| 6,067,471 A | 5/2000 | Warren |
| 6,076,014 A | 6/2000 | Alt |
| 6,449,503 B1 | 9/2002 | Hsu |
| 6,708,058 B2 | 3/2004 | Kim et al. |
| 7,085,599 B2 | 8/2006 | Kim et al. |

OTHER PUBLICATIONS

Notice of Allowance dated Nov. 15, 2004 from U.S. Appl. No. 10/121,944, 4 pages.
Office Action Response dated Jun. 28, 2004 from U.S. Appl. No. 10/121,944, 5 pages.
Office Action dated May 26, 2004 from U.S. Appl. No. 10/121,944, 4 pages.
Notice of Allowance dated May 14, 2008 from U.S. Appl. No. 11/097,458, 4 pages.
Office Action Response dated Feb. 12, 2008 from U.S. Appl. No. 11/097,458, 8 pages.
Office Action dated Dec. 26, 2007 from U.S. Appl. No. 11/097,458, 5 pages.

*Primary Examiner* — Scott M Getzow
(74) *Attorney, Agent, or Firm* — Hollingsworth & Funk, LLC

(57) ABSTRACT

A method and system for generating a characterization of one beat of a patient's supraventricular rhythm (SVR) involves performing such characterization while the heart is being paced. During SVR characterization, various pacing parameters are modified and the patient's supraventricular rhythm is characterized while the pacing parameters are modified. The SVR characterization process is effective in single and multiple chamber pacing modes.

20 Claims, 14 Drawing Sheets

Slope is flat

METHOD AND SYSTEM FOR CHARACTERIZING SUPRAVENTRICULAR RHYTHM DURING CARDIAC PACING

RELATED PATENT DOCUMENTS

This is a continuation of U.S. patent application Ser. No. 11/097,458, filed on Apr. 1, 2005, to issue as U.S. Pat. No. 7,426,411 on Sep. 16, 2008, which is a divisional of U.S. Pat. No. 6,889,079 dated May 3, 2005, to which Applicant claims priority under 35 U.S.C. § 120, and which are incorporated herein by reference.

FIELD OF THE INVENTION

The present invention relates generally to implantable medical devices and, more particularly, to generating, with an implantable medical device, a characterization of a patient's supraventricular cardiac rhythm while the heart is being paced.

BACKGROUND OF THE INVENTION

The healthy heart produces regular, synchronized contractions. Rhythmic contractions of the heart are normally controlled by the sinoatrial (SA) node, specialized cells located in the upper right atrium. The SA node is the normal pacemaker of the heart, typically initiating 60-100 heart beats per minute. When the SA node is pacing the heart normally, the heart is said to be in normal sinus rhythm (NSR).

If heart contractions are uncoordinated or irregular, the heart is denoted to be arrhythmic. Cardiac arrhythmia impairs cardiac efficiency and can be a potential life threatening event. Cardiac arrythmias have a number of etiological sources including tissue damage due to myocardial infarction, infection, or degradation of the heart's ability to generate or synchronize the electrical impulses that coordinate contractions.

Bradycardia occurs when the heart rhythm is too slow. This condition may be caused, for example, by delayed impulses from the SA node, denoted sick sinus syndrome, or by a blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid, uncoordinated contractions of the atria. Besides being hemodynamically inefficient, the rapid contractions of the atria can also adversely affect the ventricular rate. This occurs when the aberrant contractile impulses in the atria are transmitted to the ventricles. It is then possible for the aberrant atrial signals to induce ventricular tachyarrhythmias.

Ventricular tachycardia occurs, for example, when a pulse is initiated in the ventricular myocardium at a rate more rapid than the normal sinus rhythm. Ventricular tachycardia can quickly degenerate into ventricular fibrillation (VF). Ventricular fibrillation is a condition denoted by extremely rapid, nonsynchronous contractions of the ventricles. The rapid and erratic contractions of the ventricles cannot effectively pump blood to the body and the condition is fatal unless the heart is returned to sinus rhythm within a few minutes.

Implantable cardiac rhythm management systems have been used as an effective treatment for patients with serious arrhythmias. These systems typically comprise circuitry to sense signals from the heart and a pulse generator for providing electrical pulses to the heart. Leads extending into the patient's heart are connected to electrodes that contact the myocardium for sensing the heart's electrical signals and for delivering pulses to the heart in accordance with various therapies for treating the arrythmias described above.

Pacemakers may be incorporated into cardiac rhythm management systems to deliver pace pulses to the heart. Pace pulses are low energy electrical pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing the heart. Single chamber pacemakers pace and sense one heart chamber. A typical single chamber pacemaker is connected to a lead extending either to the right atrium or the right ventricle. Dual chamber pacemakers may pace and sense two chambers of the heart. A typical dual chamber pacemaker is typically connected to two leads, one lead extending to the right atrium and one lead to the right ventricle.

Pacemakers may be used to provide pacing pulses to both the left ventricle and the right ventricle. This type therapy may be used, for example, to coordinate ventricular contractions when a patient suffers from congestive heart failure (CHF). Congestive heart failure is a condition wherein the muscles of the heart deteriorate, causing the heart muscle to enlarge. Enlargement of the heart causes the contractile impulses to travel more slowly, resulting in asynchronous contractions of the left and right ventricles and reduced pumping efficiency.

Pacemakers can be programmed to provide pace pulses to the heart on demand or at a fixed rate. When a pacemaker paces the heart at a fixed rate, the pacemaker provides pace pulses to the heart without taking into account the heart's spontaneous action. In contrast, pacemakers may sense the spontaneous activity of the heart and provide pace pulses synchronized to the spontaneous activity.

For example, a single chamber ventricular pacemaker may sense and pace a ventricle. The pacemaker senses ventricular activity and provides a pace pulse to the ventricle if no spontaneous activity is sensed. If the pacemaker senses spontaneous activity, the pacing pulse is inhibited. In this example, where the pacemaker senses the ventricle, paces the ventricle and inhibits the ventricular pace pulse upon sensing a spontaneous R-wave, the pacemaker mode is denoted VVI. Alternatively, a single chamber pacemaker may sense and pace the atrium. In the case where the pacemaker senses the atrium, paces the atrium and inhibits the atrial pace pulse upon sensing a spontaneous P-wave, the pacemaker mode is denoted AAI.

A dual chamber pacemaker may be capable of sensing and pacing both the atrium and ventricle. The dual channel pacemaker is capable of using pace pulses to synchronize atrial and ventricular activity. If spontaneous cardiac activity is detected in the atrium or the ventricle, pacing pulses may be triggered or inhibited. When the pacemaker paces and senses both chambers and can trigger or inhibit pace pulses based upon sensed signals, for example, the pacemaker mode is denoted DDD. Various other configurations involving providing or inhibiting pace pulses based upon sensed cardiac events using dual or single chamber pacemakers are known in the art.

Rate adaptive pacemakers provide pacing at rates responsive to the patient's metabolic activity. Changes in metabolic activity may reflect exercise or non-exercise related changes, such as stress or excitement. The level of metabolic activity may be determined by sensing motion, respiratory rate, QT interval, venous oxygen saturation, temperature, or other patient conditions, for example. The pacemaker automatically adjusts the pacing rate to accommodate the sensed changes in the patient's condition.

Implantable cardioverter/defibrillators (ICDs) have been used as an effective treatment for patients with serious cardiac arrhythmias. For example, ICDs are capable of delivering high energy shocks to the heart, interrupting the ventricular tachyarrythmia or ventricular fibrillation and allowing the heart to resume a normal rhythm. ICDs may include pacing functions described above as well as a cardioversion/defibrillation capability.

To effectively provide treatment, a cardiac rhythm management system, such as an ICD, must identify the type of arrhythmia that is occurring and provide appropriate therapy to the heart. Arrhythmias may be effectively identified by comparing the aberrant rhythm to the patient's supraventricular conducted cardiac rhythm (SVR). For the reasons stated above, and for other reasons which will become apparent to those skilled in the art upon reading the present specification, there is a need in the art for a method that reliably and accurately characterizes a patient's supraventricular rhythm during the time the heart is being intermittently or constantly paced. The present invention fulfills these and other needs.

SUMMARY OF THE INVENTION

The present invention is directed to a method and system for generating a characterization of one beat of a patient's supraventricular rhythm (SVR) while the heart is being paced. In accordance with one embodiment of the present invention, pacing parameters are modified and the patient's supraventricular rhythm is characterized while the pacing parameters are modified.

In another embodiment of the invention, a body implantable device implements a SVR characterization method of the present invention. The body implantable system is disposed in a housing. A lead system extends from the housing into a heart and includes one or more electrodes. A detector system, coupled to the lead system, detects rate channel signals and shock channel signals sensed by the one or more electrodes. A pacemaker, coupled to the detector system, provides pacing signals to the heart. A control system is coupled to the detector system and the pacemaker. The control system controls the modification of the pacing parameters and characterizing a patient's superventricular rhythm.

In another embodiment of the invention, a system provides a means for pacing the heart, means for modifying one or more pacing parameters and means for characterizing the patient's supraventricular rhythm.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
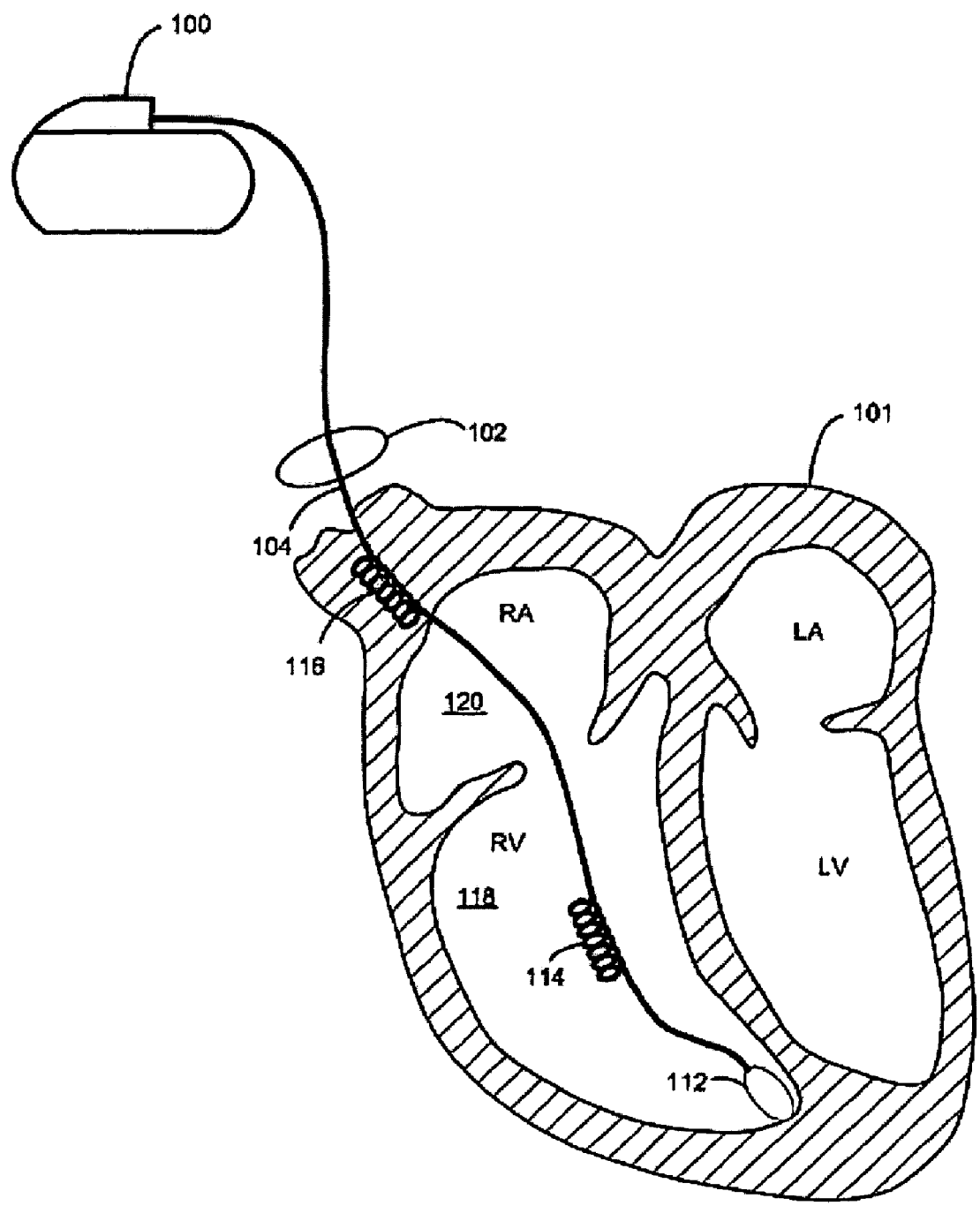
FIG. 1 is a partial view of one embodiment of a single chamber implantable cardioverter/defibrillator with an endocardial lead system extending into the right ventricle of a heart.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

A proper characterization of a patient's supraventricular conducted rhythm (SVR) requires detection of unpaced or intrinsic heartbeats. Although various methods have been proposed for characterizing a patient's SVR, these characterization methods are often dependent upon acquiring a sufficient number of intrinsic beats. One such method is described in commonly owned U.S. Pat. No. 6,708,058, which is hereby incorporated herein by reference. Another method is described in commonly owned U.S. Patent Publication No. 2003/0181818, which is hereby incorporated herein by reference.

Notwithstanding the efficacy of these approaches, additional processes may be required to obtain SVR characterization when the heart is being intermittently or constantly paced. Paced beats are not considered intrinsic beats and generally cannot be used to characterize supraventricular rhythm. Consequently, when the heart is being paced, intrinsic beats are not available for SVR characterization by previous known methods. The invention described herein provides a method of characterizing supraventricular rhythm for patients requiring intermittent or constant pacing.

The embodiments of the present system illustrated herein are generally described as being implemented in an implantable cardioverter/defibrillator (ICD), which may operate in numerous cardioversion/defibrillation and pacing modes known in the art. The systems and methods of the present invention may also be implemented in other implantable cardiac rhythm management devices that pace the heart and sense cardiac activity, such as pacemakers, for example.

In one embodiment, the cardiac rhythm management system is an implantable cardioverter/defibrillator configured as a single chamber device that operates to generate a characterization of one beat of a patient's supraventricular rhythm in accordance with the principles of the present invention. In another embodiment, the cardiac rhythm management system is an implantable cardioverter/defibrillator that is configured as a dual chamber device. In yet another embodiment, the cardiac rhythm management system is an implantable cardioverter/defibrillator configured to provide pacing pulses to both ventricles of the heart, as in a congestive heart failure (CHF) device.

Various types of single and multiple chamber cardiac rhythm management systems are known in the art. The present cardiac rhythm management system may be implemented in various implantable atrial or ventricular rhythm management systems, which may include numerous pacing modes known in the art. The systems and methods of the present invention may be implemented in external cardioverter/monitor systems. Furthermore, although the present system is described in conjunction with an implantable cardioverter/defibrillator (ICD) having a microprocessor-based architecture, it will be understood that the cardiac rhythm management system may be implemented in any logic-based integrated circuit architecture, if desired.

The present invention provides systems and methods for monitoring a patient's electrocardiogram and producing a characterization of the patient's supraventricular rhythm while the heart is being intermittently or constantly paced. Producing such a characterization may be effected for a number of different purposes. By way of example, the diagnosis of a patient's cardiac rhythms may be enhanced by comparing QRS complexes of a current cardiac rhythm to a characterization of the patient's supraventricular rhythm produced by employment of the methodologies of the present invention. By way of further example, the titration of drug dosage based on electrocardiographic properties of such a snapshot produced in accordance with the present invention may also be enhanced.

The methods of producing an accurate characterization of a patient's normal cardiac rhythm may be used in combination with various cardiac rhythm management systems, such as, for example, an automatic VT/SVT (ventricular tachyarrhythmia/supraventricular tachyarrhythmia) rhythm discrimination technique employed in an implantable cardioverter/defibrillator (ICD). Also, the methodologies of the present invention may be used as a component of an automatic Holter analysis system employed in an implantable pacemaker, for example. These and other applications may be enhanced by employment of the systems and methods of the present invention.

Referring now to FIG. 1 of the drawings, there is shown one embodiment of a cardiac rhythm management system that includes an implantable cardioverter/defibrillator (ICD) 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electric cardiac signals produced by the heart 101 and to provide electrical energy to the heart 101 under predetermined conditions to treat cardiac arrhythmias of the heart 101. The electrical energy provided may be in the form of low energy pacing pulses or high energy pulses for cardioversion or defibrillation. The system depicted in FIG. 1 is a single chamber device, capable of sensing signals produced by the right ventricle and providing pacing and cardioversion/defibrillation signals to the right ventricle of the heart. In an embodiment in which only pacing is performed, the cardioverter/defibrillator system 100 need not provide for generation of high energy pulses.

The intracardiac lead system 102 may include one or more pacing electrodes and one or more intracardiac defibrillation electrodes. In the particular embodiment shown in FIG. 1, the intracardiac lead system 102 includes a right ventricular lead system 104. The right ventricular lead system 104 includes an SVC-coil 116, an RV-coil 114, and an RV-tip electrode 112. The RV-coil 114, which is also referred to as an RV-ring electrode, is spaced apart from the RV-tip electrode 112, which is a pacing electrode. In one embodiment, the right ventricular lead system 104 is configured as an integrated bipolar pace/shock lead. The can electrode may be used in combination with, or as an alternate to, the SVC-coil electrode 116.

In the configuration of FIG. 1, the intracardiac lead system 102 is positioned within the heart 101, with a portion of the right ventricular lead system 104 system extending through the right atrium 120 into the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

Figure 2:
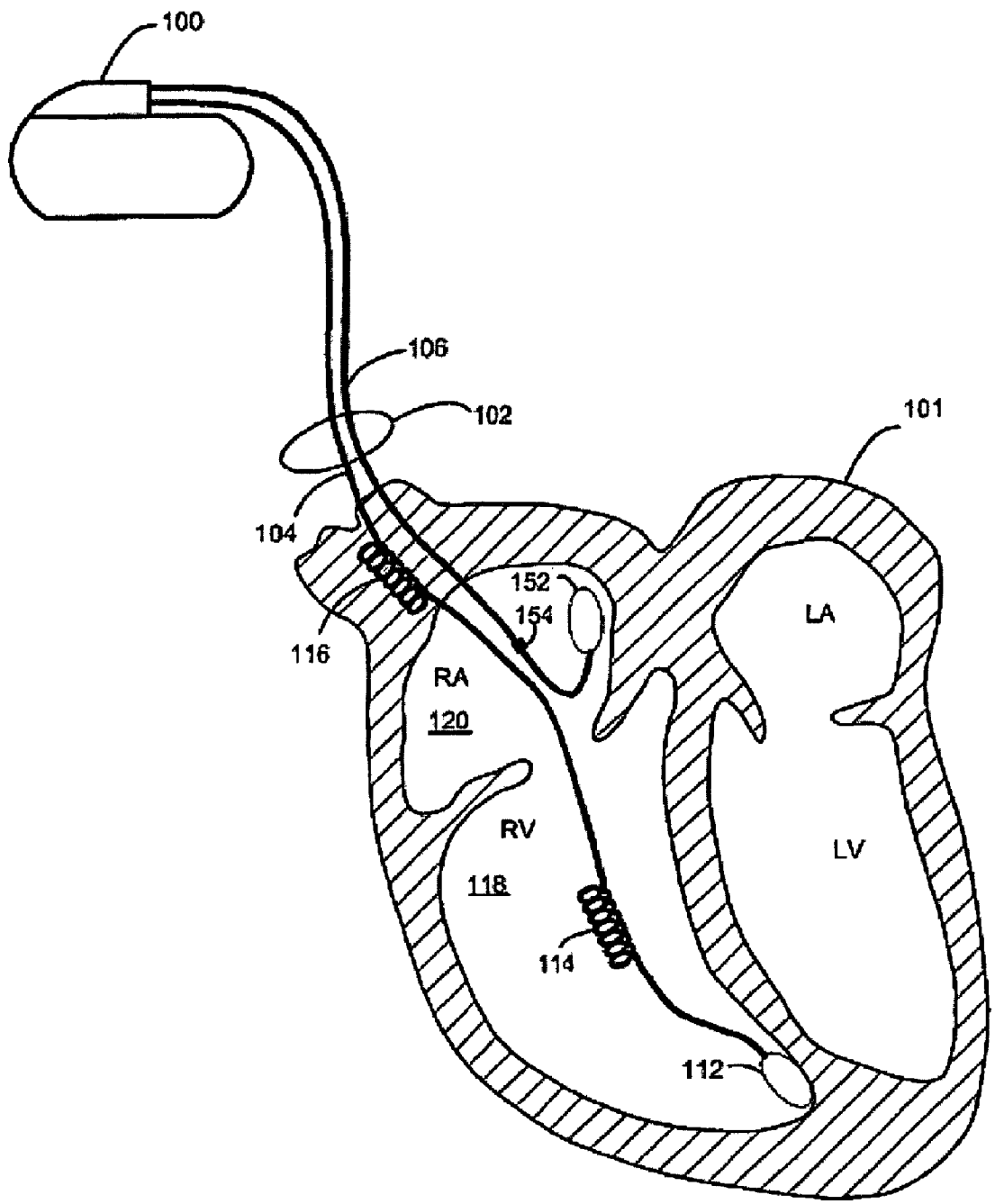
FIG. 2 is a partial view of one embodiment of a dual chamber implantable cardioverter/defibrillator with an endocardial lead system extending into right atrial and right ventricular chambers of a heart.

FIG. 2 depicts another embodiment of an implantable cardioverter/defibrillator in accordance with the invention. The device of this embodiment includes an ICD 100 electrically and physically coupled to an intracardiac lead system 102 which extends into a human body and into a heart 101. In the particular embodiment shown in FIG. 2, the device is a dual chamber device. A dual chamber device is capable of sensing signals from the right atrium and right ventricle and providing pacing pulses or cardioversion/defibrillation pulses to the right atrium and the right ventricle. The intracardiac lead system 102 includes a right ventricular lead system 104 and a right atrial lead system 106. Similarly to the single chamber device, the right ventricular lead system 104 includes an SVC-coil 116, an RV-coil 114, and an RV-tip electrode 112. The atrial lead system 106 includes an A-tip electrode 152 and an A-ring electrode 154. In one embodiment, the atrial lead system 106 is configured as an atrial J lead.

In the configuration of FIG. 2, the intracardiac lead system 102 is positioned within the heart 101, with a portion of the atrial lead system 106 extending into the right atrium 120 and portions of the right ventricular lead system 104 system extending through the right atrium 120 into the right ventricle 118. The A-tip electrode 152 and A-ring electrode 154 are positioned at appropriate locations within the right atrium 120. The RV-tip electrode 112 and RV-coil 114 are positioned at appropriate locations within the right ventricle 118. The SVC-coil 116 is positioned at an appropriate location within the right atrium chamber 120 of the heart 101 or a major vein leading to the right atrium chamber 120 of the heart 101.

Figure 3:
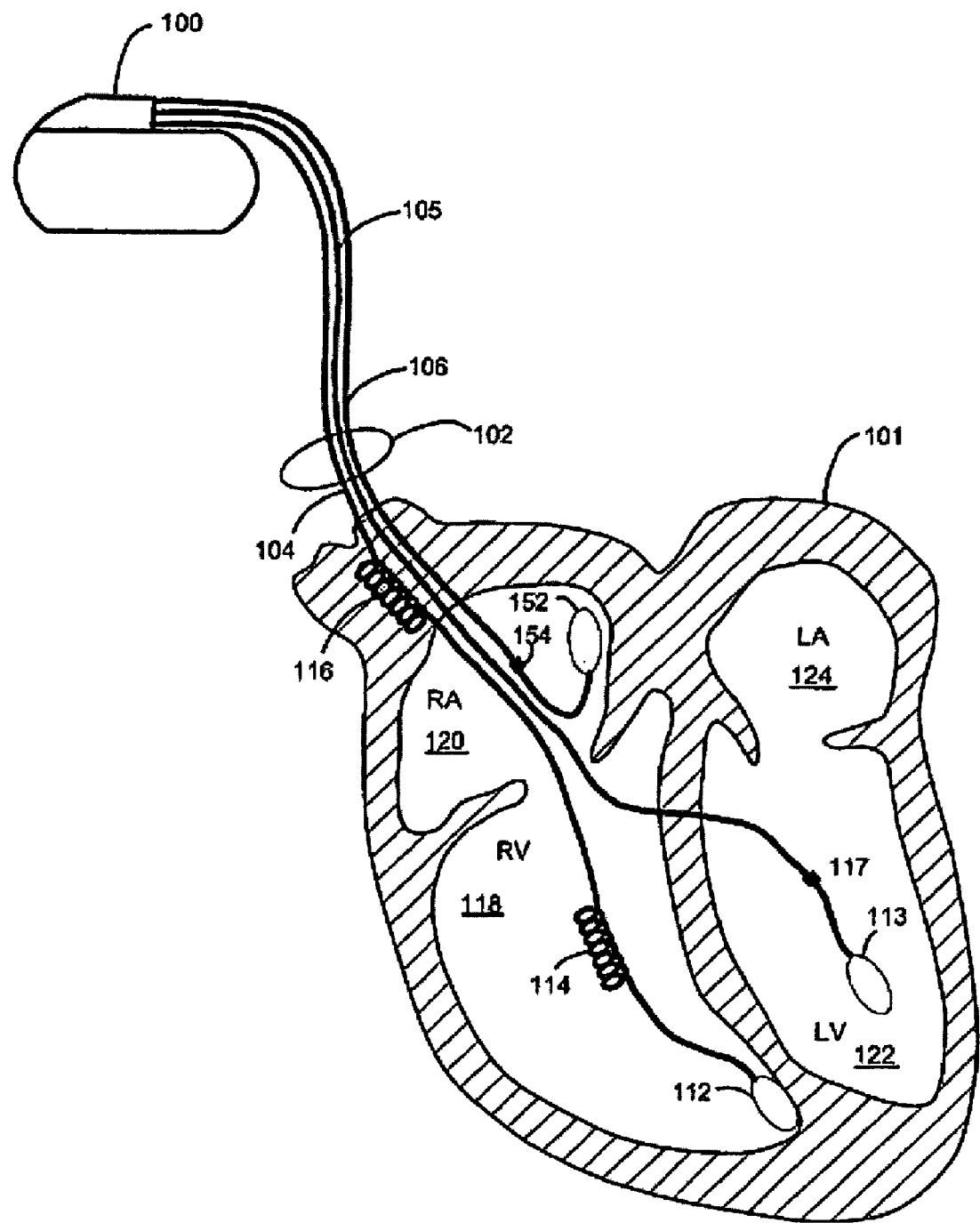
FIG. 3 is a partial view of one embodiment of an implantable cardioverter/defibrillator with an endocardial lead system extending into the right atrium and the right and left ventricles of a heart.

In another embodiment of the invention, and with reference to FIG. 3 of the drawings, there is shown an implantable cardioverter/defibrillator that includes an implantable cardiac rhythm management system 100 coupled to an intracardiac lead system 102 which comprises right ventricle, left ventricle and right atrial leads 104, 105, 106, respectively. In this configuration, the device may be used as a congestive heart failure (CHF) device, capable of sensing signals from the right atrium and the right ventricle and providing pacing and cardioversion/defibrillation pulses to the right atrium and the left and right ventricles. This system may be used, for example, to coordinate biventricular pacing for patients with congestive heart failure.

The intracardiac lead system 102 for the particular embodiment shown in FIG. 3 includes a right ventricular lead system 104, a left ventricular lead system 105, and a right atrial lead system 106. The right atrial lead system 106 extends into the right atrium 120 and includes an A-tip electrode 152 and A-ring electrode 154 positioned at appropriate locations within the right atrium 120. The right ventricular lead system 104 includes an SVC-coil 116, an RV-coil 114, and an RV-tip electrode 112. The left ventricular lead system 105 includes a LV ring 117 and an LV-tip electrode 113. The intracardiac lead system 102 is positioned within the heart 101, with a portion of the right ventricular lead system 104 system extending through the right atrium 120 into the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 3 are defibrillation coils. The LV-tip electrode 113 and LV-ring electrode 117 may be advanced through the superior vena cava, the right atrium, the valve of the coronary sinus, the coronary sinus, and into a coronary vein communicating with the coronary sinus, such as the great vein, and are positioned to provide pacing and defibrillation signals in the left ventricle 122.

Additional configurations of sensing, pacing and defibrillation electrodes can be included in the intracardiac lead system 102 to allow for various bipolar sensing, pacing, and defibrillation capabilities. The cardiac rhythm management system may also comprise a can electrode (not shown). Other intracardiac lead and electrode arrangements and configurations known in the art are also possible and considered to be within the scope of the present system.

Figure 4:
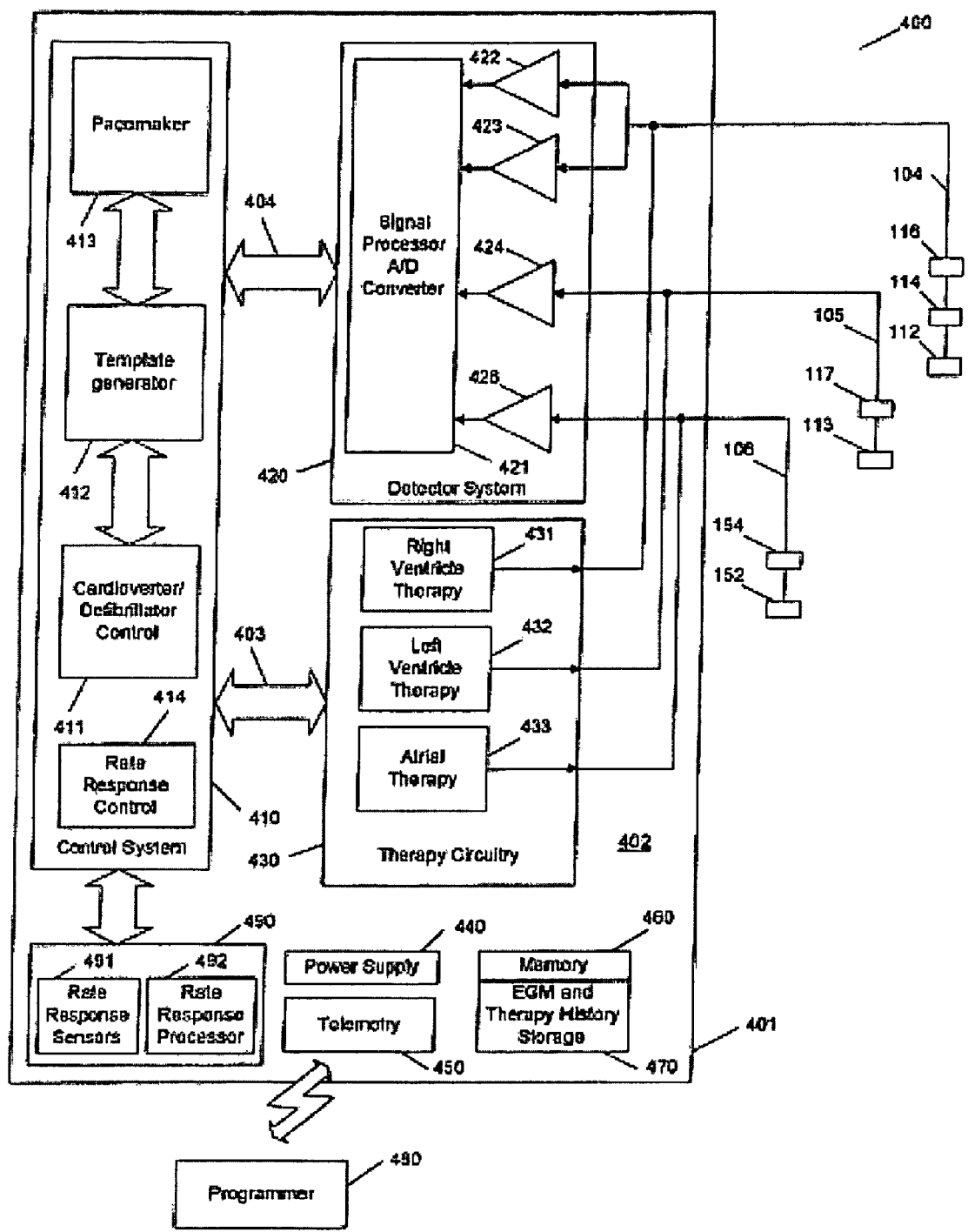
FIG. 4 is a block diagram of an implantable cardioverter/defibrillator with which SVR characterization of the present invention can be implemented.

Referring now to FIG. 4, there is shown a block diagram of an embodiment of a cardiac rhythm management system 400 configured as an ICD suitable for implementing the SVR characterization methodology of the present invention. FIG. 4 shows the cardiac rhythm management system divided into functional blocks. It is understood by those skilled in the art that there exist many possible configurations in which these functional blocks can be arranged. The example depicted in FIG. 4 is one possible functional arrangement. The cardiac rhythm management system 400 includes cardiac rhythm management circuitry 402 for receiving cardiac signals from a heart 101 (not shown in FIG. 4) and delivering electrical energy in the form of pace pulses or cardioversion/defibrillation pulses to the heart. The cardiac rhythm management system 400 includes an intracardiac lead system with right ventricular lead 104, left ventricular lead 105, and right atrial lead 106 as previously discussed.

In one embodiment, the cardiac rhythm management circuitry 402 is encased and hermetically sealed in a housing 401 suitable for implanting in a human body as is known in the art. Power to the cardiac rhythm management system 400 is supplied by an electrochemical battery 440 housed within the cardiac rhythm management system 400. A connector block (not shown) is additionally attached to the housing 401 of the cardiac rhythm management system 400 to allow for the physical and electrical attachment of the intracardiac lead system conductors to the cardiac rhythm management system circuitry 402.

In one embodiment, the cardiac rhythm management circuitry 402 is a programmable microprocessor-based system, with a control system 410 and a memory circuit 460. The memory circuit contains parameters for various pacing, defibrillation, and sensing modes and stores data indicative of cardiac signals received by other components of the cardiac rhythm management circuitry 402. The control system 410 and memory circuit 460 cooperate with other components of the cardiac rhythm management circuitry 402 to perform operations involving the characterization of a patient's supraventricular rhythm according to the principles of the present invention, in addition to other sensing, pacing and defibrillation functions. Data storage is also provided for storing historical EGM and therapy data 470, which may be used for various purposes and transmitted to an external programmer unit 480 as needed or desired.

The cardiac rhythm management circuitry may also include a rate responsive subsubsystem 490, comprising one or more rate response sensors 491 and associated rate response processing circuitry 492 for detecting and assessing patient heart rate demand. The rate responsive subsystem is coupled to a rate response control section 414 of the control system 410 to facilitate rate-adaptive pacing. The rate responsive subsystem 490 may also be used to determine the physiologic heart rate demand of the patient for the purposes of SVR characterization. The rate response sensors 491 may include several types, for example, accelerometers or vibration sensors to sense patient physical activity, sensors to determine respiration demand (e.g. minute ventilation), or other sensor types known in the art. The output of one or more types of rate response sensors 491 may be used in response to a combination of various patient conditions to enhance physiologic operation of the pacemaker 413.

The rate responsive subsystem 490 may be implemented to provide a signal indicating the heart rate demand of the patient. In one example, the rate responsive subsystem 490 may provide a numerical output to the pacemaker 413 indicating a number of beats per minute above a programmed lower rate limit (LRL) at which the heart should be paced in response to the sensor-determined heart rate demand. Alternatively, a numerical output may be provided to the pacemaker 413 indicating a decrease in cardiac cycle interval that should be provided. For the purposes of SVR characterization, the rate responsive subsystem 490 may be adapted to indicate a level of physiologic heart rate demand that is sufficiently low for SVR characterization to be attempted.

Telemetry circuitry 450 is additionally coupled to the cardiac rhythm management circuitry 402 to allow the cardiac rhythm management system 400 to communicate with an external programmer unit 480. In one embodiment, the telemetry circuitry 450 and the programmer unit 480 use a wire loop antenna and a radio frequency telemetric link, as is known in the art, to receive and transmit signals and data between the programmer unit 480 and telemetry circuitry 450. In this manner, programming commands and data are transferred between the cardiac rhythm management circuitry 402 and the programmer unit 480 during and after implant.

The programming commands allow a physician to set or modify various parameters used by the cardiac rhythm management system. These parameters may include setting the pacing mode, the AV delay, and one or more upper or lower pacing limits, for example, as well as various other parameters that optimize the operation of the cardiac rhythm system for a particular patient's conditions. Further, programming commands may allow a physician to set or modify various parameters used in connection with characterization of the patient's supraventricular rhythm, for example, setting an independent rate limit, changing the pacing rate a predetermined number of beats per minute during SVR characterization, increasing the lower rate interval by a predetermined time interval during SVR characterization and/or decreasing the lower rate limit by a predetermined percentage. Other programmable parameters applicable to SVR characterization may include the rate of transition of pacing rate, the rate of transition of AV delay, and the total number of beats for which pacing parameter modification is allowed during SVR characterization. In addition, the cardiac rhythm management system 400 may download to the programmer unit 480 stored cardiac data pertaining to SVR characterization information, sensed arrhythmic episodes within the heart, and subsequent therapy or therapies applied to correct the sensed arrhythmic event.

Cardiac signals are sensed through the electrodes positioned within the heart. Cardiac signals sensed through use of the RV-tip electrode 112 or LV-tip electrode 113 are near-field signals or rate channel signals as are known in the art. A right ventricle rate channel signal may be detected as a voltage developed between the RV-tip electrode 112 and the RV-coil 114. In the embodiment of the cardiac defibrillator 100 depicted in FIG. 4, RV-tip and RV-coil electrodes 112, 114 are shown coupled to a V sense amplifier 422 provided within the detector system 420. Right ventricle rate channel signals received by the V sense amplifier 422 are communicated to the signal processor and analog-to-digital (A/D) converter 421. The V sense amplifier 422 serves to sense and amplify the right ventricle rate channel signals. The signal processor and A/D converter 421 converts the signals from analog to digital form and communicates the signals to the control system 410.

A left ventricle rate channel signal may be detected as a voltage developed between the LV-tip electrode 113 and the LV-ring electrode 117. In the embodiment of the cardiac defibrillator 100 depicted in FIG. 4, LV-tip and LV-ring electrodes 113, 117 are shown coupled to a V sense amplifier 424 provided within the detector system 420. Left ventricle rate channel signals received by the V sense amplifier 424 are communicated to the signal processor and analog-to-digital (A/D) converter 421. The V sense amplifier 424 serves to sense and amplify the left ventricle rate channel signals. The signal processor and A/D converter 421 converts the signals from analog to digital form and communicates the signals to the control system 410.

Cardiac signals sensed through use of the defibrillation coils or electrodes 114, 116 are far-field signals, also referred to as morphology or shock channel signals, as are known in the art. More particularly, a right ventricle shock channel signal may be detected as a voltage developed between the RV-coil 114 and the SVC-coil 116. A shock channel signal may also be detected as a voltage developed between the RV-coil 114 and can electrode (not shown). Right ventricle shock channel signals developed using appropriate combinations of the RV-coil 114, SVC-coil 116, and can electrode (not shown) are sensed and amplified by a right ventricle shock EGM amplifier 423 located in the detector system 420. The output of the right ventricle shock EGM amplifier 423 is coupled to the signal processor and A/D converter 421 in the detector system 420.

A-tip and A-ring electrodes 152, 154 are shown coupled to an A-sense amplifier 426 located within the detector system 420. Atrial sense signals received by the A-sense amplifier 426 in the detector system 420 are communicated to the A/D converter 421. The A-sense amplifier serves to sense and amplify the A-wave signals. The A/D converter 421 converts the sensed signals from analog to digital form and communicates the signals to the control system 410.

The pacemaker circuitry 413 located within the control system 410 may communicate pacing signals to the RV-tip, LV-tip and A-tip electrodes 112, 113 and 152, respectively, according to a preestablished pacing regimen under appropriate conditions. Control signals, developed in accordance with a pacing regimen, are initiated in the pacemaker 413 and transmitted to the therapy circuitry 430 where pacing pulses are generated. In one example, pacing pulses may be provided to the right ventricle by the right ventricle therapy circuit 431, to the left ventricle by the left ventricle therapy circuit 433, and/or to the right atrium by the atrial therapy circuit 432. A pacing regimen may be modified by the control system to facilitate the SVR characterization in accordance with the invention.

Cardioversion/defibrillation control signals may be developed in the cardioverter/defibrillation control system 411 to initiate a high energy pulse. The high energy cardioversion/defibrillation pulses may be generated by the therapy circuitry 430 in response to detection of fibrillation or tachycardia.

The cardiac rhythm management system 400 depicted in FIG. 4 is well-suited for implementing SVR characterization according to the principles of the present invention. In the embodiment shown in FIG. 4, the SVR characterization processes of the present invention are largely controlled by template generator 412. The shock channel and rate channel signals are sensed by appropriate electrodes and amplified by the EGM and V sense amplifiers as described above. These signals are transferred through the signal processor and A/D converter 420 and to the template generator 412. It is understood that the required shock and rate channel signals may be developed and processed by components other than those depicted in FIG. 4 for system architectures that differ from the system architectures described herein.

SVR characterization may be performed either automatically or upon command. SVR characterization upon command typically includes the supervision of a physician who controls the SVR characterization process through programmable pacemaker features available through the programmer. Commanded SVR characterization may be performed with or without pacing parameter modification.

Figure 5:
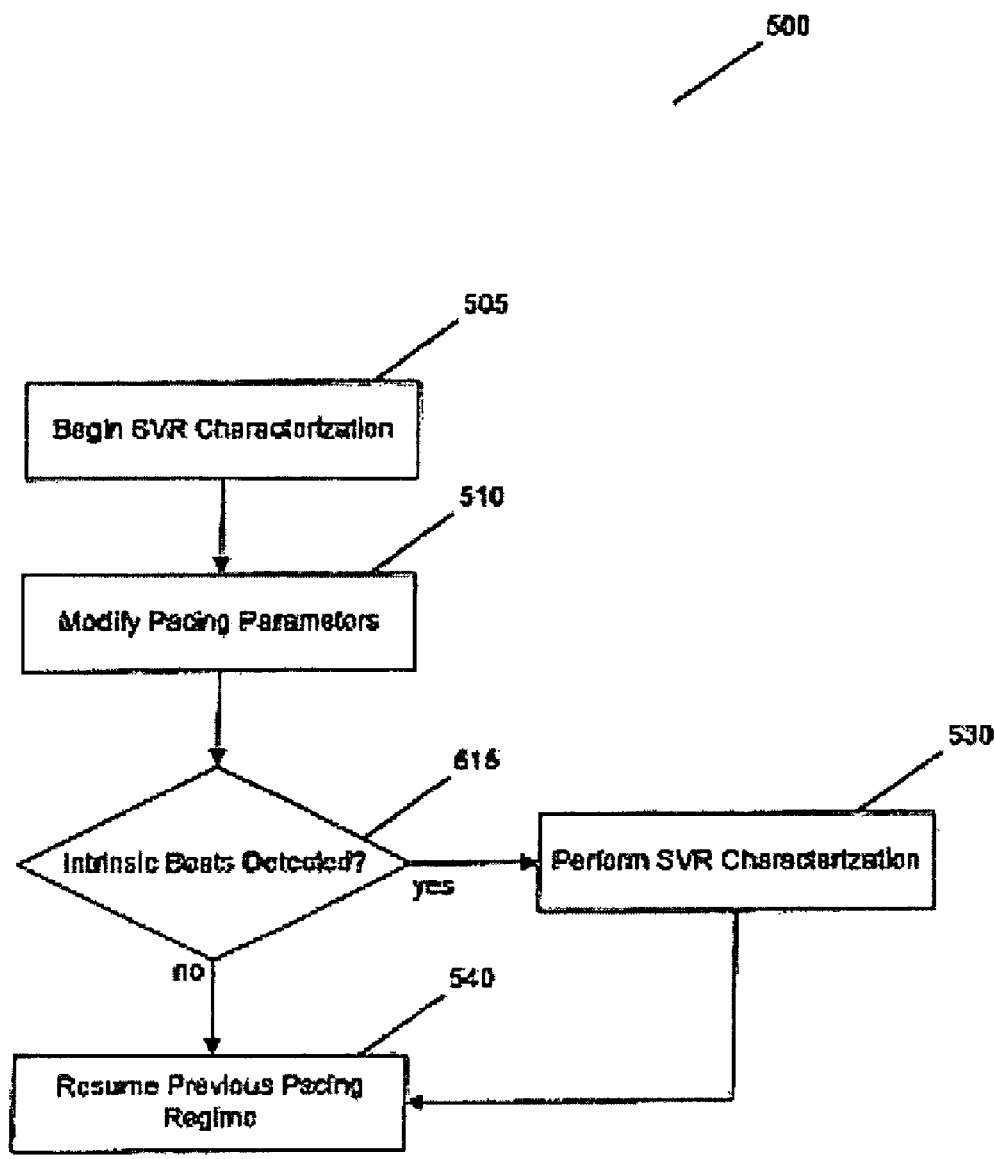
FIG. 5 is a flowchart of a method of characterizing supraventricular rhythm when the heart is being paced in accordance with an embodiment of the present invention.

FIG. 5 is a flowchart illustrating, in broad and general terms, various processes for characterizing a patient's supraventricular rhythm according to an embodiment of the present invention. Prior to SVR characterization by a method of the invention, it is assumed that the patient's heart is being intermittently or constantly paced with pacing pulses developed in the cardiac rhythm management system and applied to one or more of the heart chambers through the lead system as described above. Upon commencement of SVR characterization 505, one or more pacing parameters are modified 510. The one or more pacing parameters may be modified to alter the pacing mode, including tracking and rate responsiveness, and/or one or more pacing timing intervals, for example. The pacing parameters may be modified 510 abruptly, or gradually within a particular time interval, or incrementally each beat. Modification of the one or more pacing parameters and timing intervals may allow for the development of intrinsic beats. If a sufficient number of intrinsic beats are detected 515 during the time the pacing parameters are modified, SVR characterization is performed 530. Following successful SVR characterization, the previous pacing regime is resumed 540. If intrinsic beats are not detected 515 following modification of the pacing parameters, SVR characterization is unsuccessful and the previous pacing regimen is resumed 540.

Figure 6:
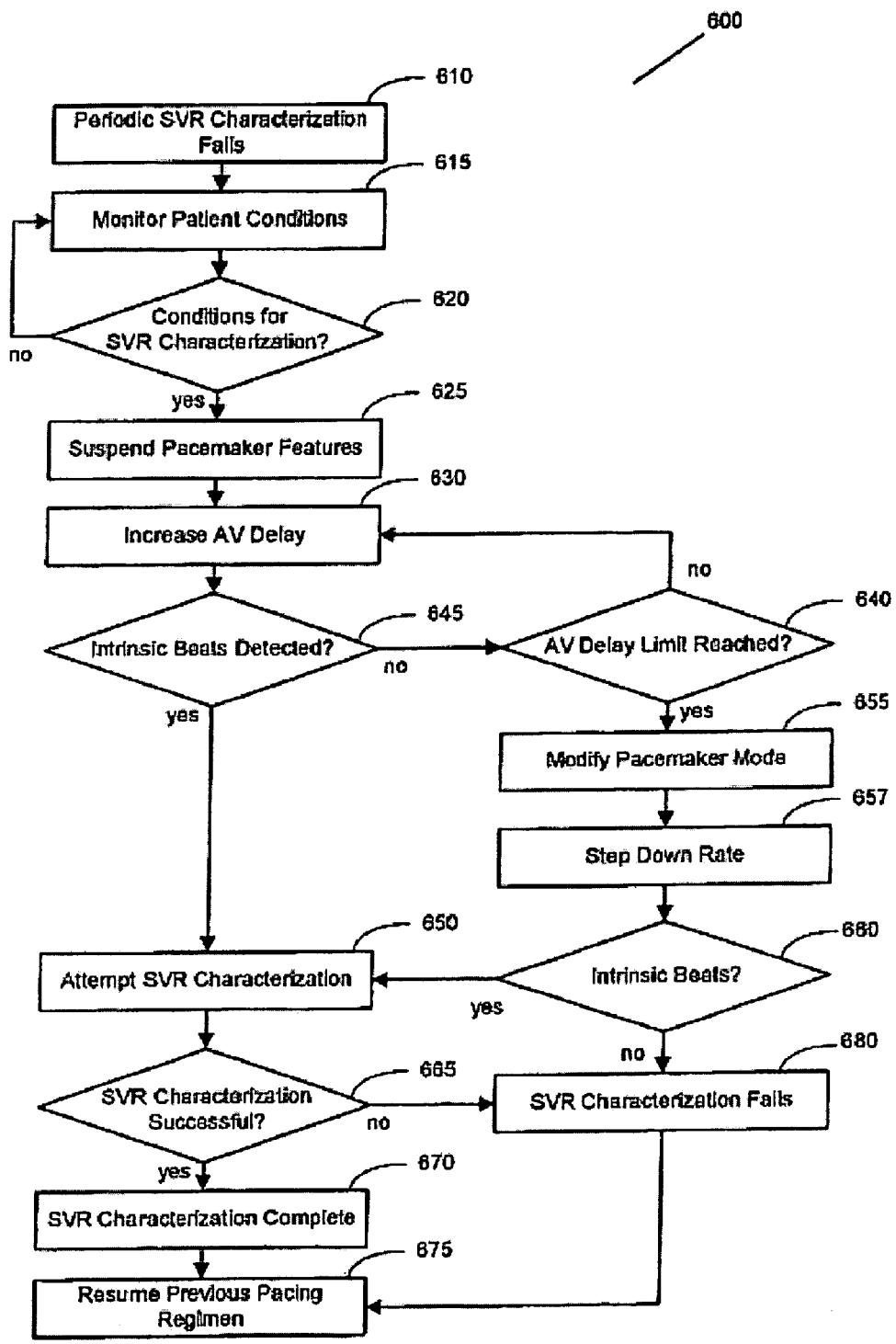
FIG. 6 is a flowchart of a method of characterizing supraventricular rhythm when two chambers of the heart are paced in accordance with an embodiment of the present invention.

Turning now to FIG. 6, various processes are illustrated for characterization of one beat of a patient's supraventricular rhythm according to another embodiment of the present invention. In this exemplary embodiment, a dual chamber device, such as the one illustrated in FIG. 2, senses and paces the heart. The dual chamber device shown is capable of pacing and sensing both the right atrium and the right ventricle. As previously discussed, prior to SVR characterization, various pacing parameters may be set by the programmer. In one embodiment of the invention, SVR characterization without pacing modification, denoted passive SVR characterization, may be attempted periodically. Successful passive SVR characterization is dependent on acquiring a sufficient number of intrinsic beats with which to characterize the patient's supraventricular rhythm. However, when the heart is being constantly or intermittently paced, passive SVR characterization may fail due to a lack of intrinsic beats.

According to the method of the present invention depicted in FIG. 6, if passive SVR characterization fails 610, SVR characterization with pacing modification, denoted active SVR characterization, may automatically be attempted. Automatic, active SVR characterization modifies pacing parameters to elicit intrinsic beats when patient conditions are appropriate for SVR characterization and previous passive SVR characterization attempts have been unsuccessful. An exemplary set of patient conditions that must typically be present for automatic, active SVR characterization to occur include the following conditions: 1) rate response sensors indicate low patient physiologic heart rate demand, 2) time of day window indicates usual time for low patient activity, e.g., 1 a.m. to 4 a.m., 3) V rate is very low, e.g., in the lowest quartile of the range of rates detected over the past 24 hours, 4) SVR characterization has not been performed for more than a predetermined period, e.g., 24 hours, or other time period. Attempting SVR characterization according to a non-24 hour period may also be useful to allow SVR characterization attempts to occur at different times throughout the day. The probability of successful SVR characterization may be increased if attempts are made with varying physiological conditions over the diurnal cycle. Other combinations of the conditions listed above and other patient conditions may also be used to determine when automatic, active SVR characterization may occur.

The patient's conditions are monitored 615 and if the conditions indicate that active SVR characterization can be attempted 620, the pacemaker features that may interfere with SVR characterization are suspended 625. An exemplary set of pacemaker features that may be suspended during pace parameter modification include, for example: 1) dynamic AV delay, 2) dynamic post ventricular refractory period (PVARP), 3) AV search hysteresis, 4) rate hysteresis offset, 5) sensed AV delay offset, 6) PVARP after premature ventricular complex (PVC), 7) dynamic ventricular refractory period (VRP), and 8) ventricular rate regularization (VRR).

Pacing parameters may be modified by increasing the AV delay 630, by a predetermined amount each beat until an AV delay limit is reached 640. In one embodiment, the AV delay is increased by approximately 25 ms each beat until the AV delay reaches a limit of approximately 400 ms. During the time the AV delay interval is modified, SVR characterization is attempted 650 if a predetermined number of consecutive intrinsic beats is detected 645, for example, four consecutive intrinsic beats. If SVR characterization is successful 665, SVR characterization is complete 670 and the previous pacing regimen is resumed 675.

If a sufficient number of intrinsic beats is not detected 645 after increasing the AV delay interval to the AV delay interval limit 640, the pacing mode may be modified 655. For example, the pacing mode may be modified from a dual chamber pacing mode to a single chamber pacing mode, or to a non-tracking, non-rate responsive mode. The pacing rate may be stepped down 657 incrementally to a lower rate limit (LRL) to elicit intrinsic beats.

If a predetermined number of intrinsic beats is detected 660 while the pacing mode is modified, SVR characterization is attempted 650. If SVR characterization is successful 665, SVR characterization is complete 670 and the previous pacing regimen is resumed 675. If a sufficient number of intrinsic beats is not detected 660 after the pacing mode is modified, SVR characterization fails 680 and the previous pacing regimen 675 is resumed without SVR characterization.

Automatic SVR characterization may be terminated prior to completion if predetermined patient conditions are detected. If automatic SVR characterization is terminated, the previous pacing regimen is resumed. Patient conditions which terminate modified pacing parameters and automatic SVR characterization include, for example: 1) the patient's physiologic heart rate demand increases beyond acceptable limit, 2) a predetermined number of beats with modified pacing parameters is exceeded, 3) the patient's average heart rate becomes elevated, or 4) a predetermined number of paced beats are seen after pacing parameter modifications are made.

Figure 7:
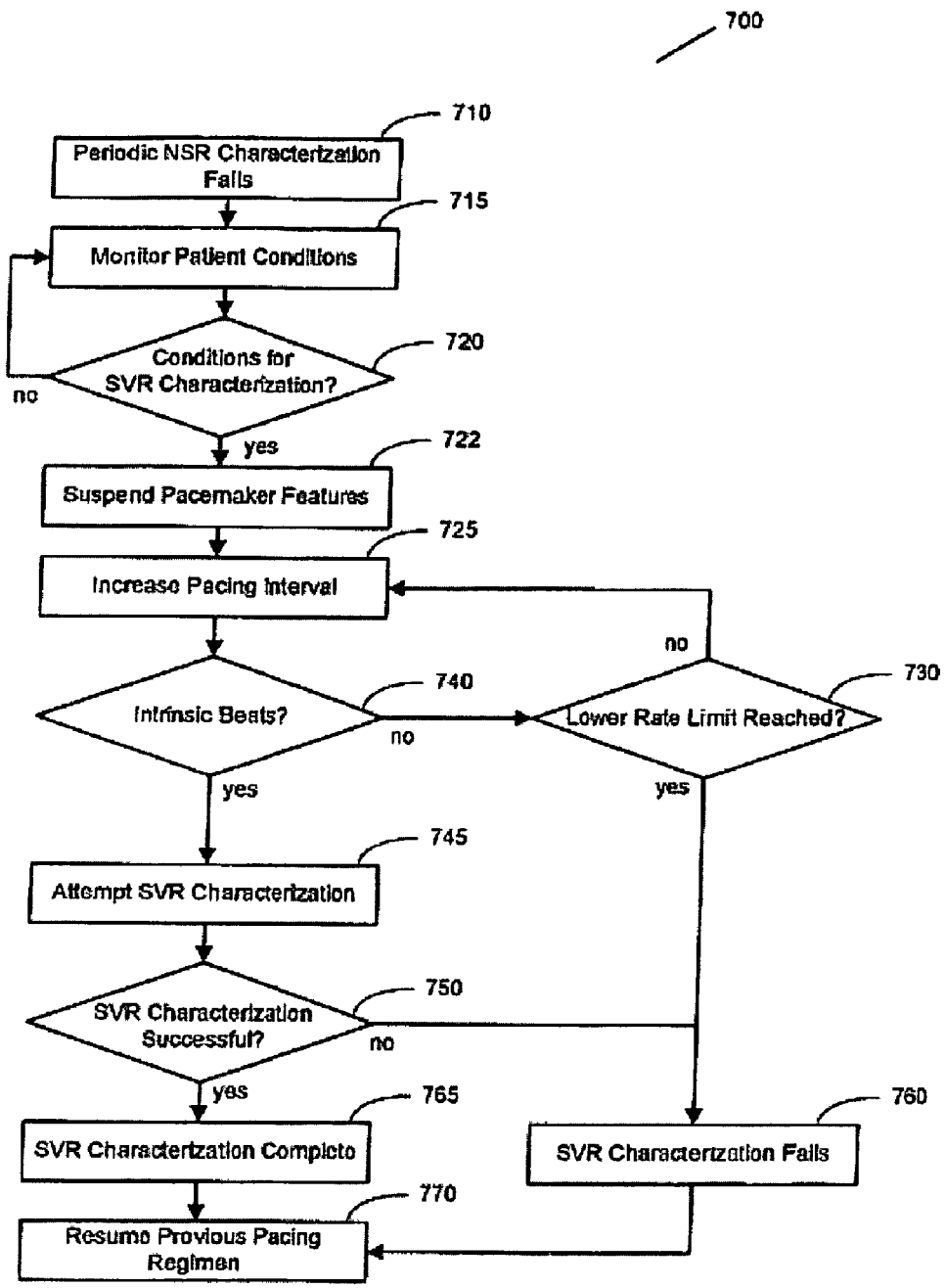
FIG. 7 is a flowchart of a method of characterizing supraventricular rhythm when one chamber of the heart is paced in accordance with an embodiment of the present invention.

Turning now to FIG. 7, various processes are illustrated for characterization of a patient's supraventricular rhythm according to another embodiment of the present invention. In this exemplary embodiment, a single chamber device, such as the one shown in FIG. 1, paces the heart. The single chamber device is assumed capable of pacing and sensing the right ventricle. Prior to SVR characterization, various pacing parameters may be set up by the programmer as previously discussed. Passive SVR characterization may be attempted periodically. However, if the heart is being intermittently or constantly paced, passive SVR characterization may fail 710 due to a lack of a sufficient number of intrinsic beats. If passive SVR characterization fails, the patient conditions are monitored 715 to determine an appropriate time to attempt active SVR characterization with pacing modification. Patient conditions that must be present for active SVR characterization are those previously specified for the dual chamber device.

If patient conditions indicate that active SVR characterization can be attempted 720, the pacemaker features that may interfere with SVR characterization are suspended 722. An exemplary set of pacemaker features that may be suspended during pace parameter modification include, for example: 1) rate hysteresis offset, 2) dynamic ventricular refractory period (VRP), and 3) ventricular rate regularization. Pacing parameters are modified by incrementally increasing the pacing interval 725 by a predetermined amount each beat until a lower rate limit is reached 730. In one embodiment, the V-V interval is incrementally increased by approximately 100 ms each beat until a lower rate limit, such as approximately 45 bpm is reached. If a predetermined number of intrinsic beats is detected 740 while the pacing parameters are modified, SVR characterization is attempted 745. If SVR characterization is successful 750, the SVR characterization is complete 765 and the previous pacing regimen is resumed 770. If the SVR characterization attempt is not successful 750, or if the predetermined number of intrinsic beats is not detected 740 before the lower rate limit is reached 730, SVR characterization fails 760 and the previous pacing regimen is resumed 770 without SVR characterization. Automatic, active SVR characterization may be terminated prior to completion if predetermined patient conditions are detected. In this event, the previous pacing regimen is resumed. Patient conditions which terminate modified pacing parameters and SVR characterization are those previously discussed in connection with the dual chamber device.

Figure 8:
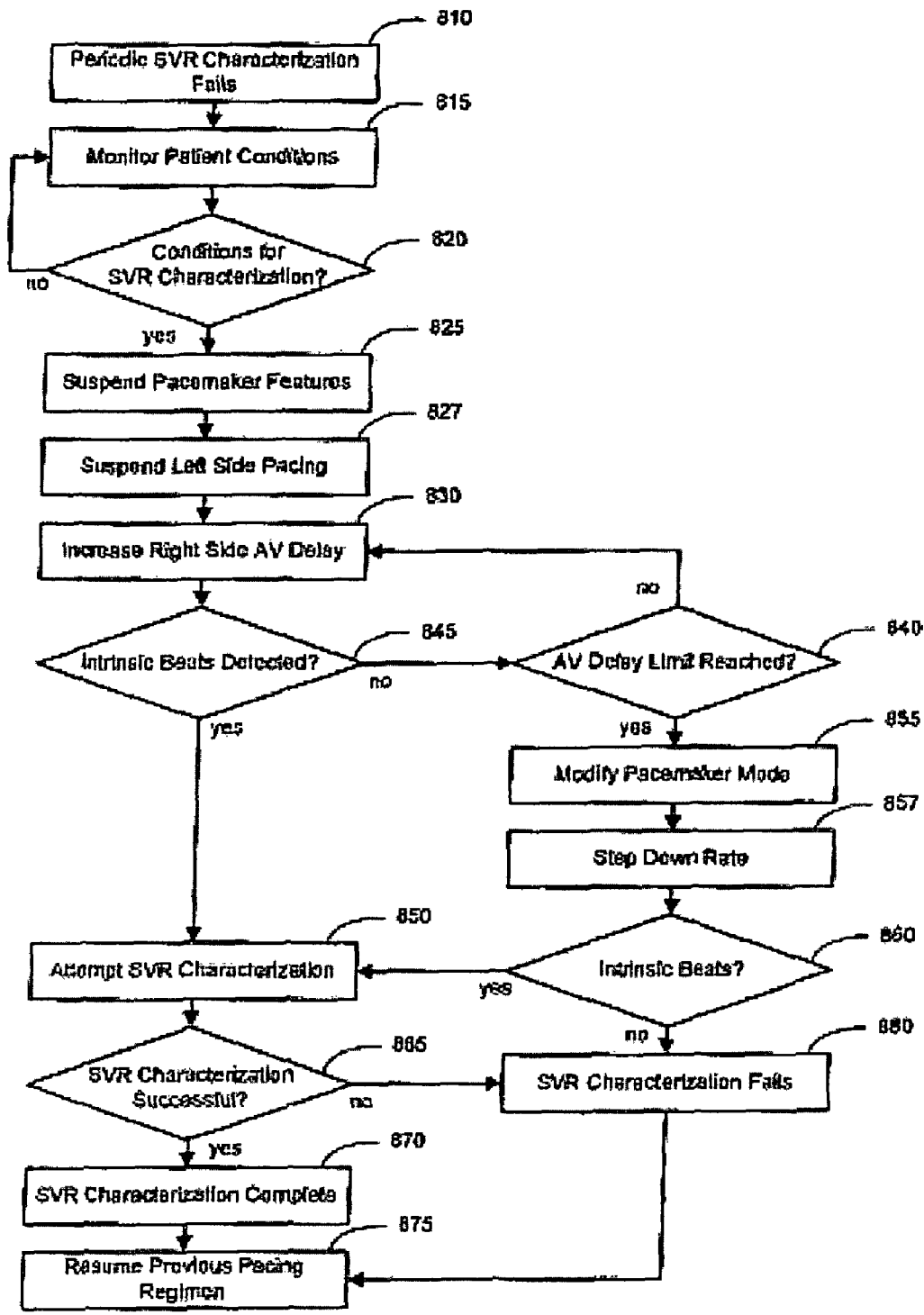
FIG. 8 is a flowchart of a method of characterizing supraventricular rhythm when both ventricles of the heart are paced in accordance with an embodiment of the present invention.

Referring to FIG. 8, a process for characterization of supraventricular rhythm is illustrated when a multi-chamber, biventricular device paces the heart, such as a CHF device. The CHF device is capable of pacing the left ventricle, the right ventricle, and the right atrium. The CHF device may pace both ventricles, for example, to provide biventricular coordination for a patient with congestive heart failure.

Prior to SVR characterization, various pacing parameters may be set up by the programmer as previously discussed. If the periodic passive SVR characterization fails 810, active SVR characterization may be automatically initiated when patient conditions are appropriate for active SVR characterization. The patient's conditions are monitored 815, and if patient conditions indicate that active SVR characterization can be attempted 820, the pacemaker features that interfere with SVR characterization are suspended 825. The left side pacing of the heart may also be suspended 827. Pacing parameters are modified by increasing the AV delay 830, by a predetermined amount each beat until an AV delay limit is reached 840. In one embodiment, the AV delay is increased by approximately 25 ms each beat until the AV delay reaches a limit of approximately 400 ms. During the time the AV delay interval is modified, if a predetermined number of consecutive intrinsic beats is detected 845, for example, four consecutive intrinsic beats, SVR characterization is attempted 850. If SVR characterization is successful 865, SVR characterization is complete 870 and the previous pacing regimen is resumed 875.

If no intrinsic beats are detected 845 after increasing the AV delay interval 830 to the AV delay interval limit 840, the pacing mode may be modified 855. For example, the pacing mode may be modified from a dual chamber pacing mode to a single chamber pacing mode or to a non-tracking, non-rate responsive mode. The pacing rate may be stepped down 857 incrementally to a lower rate limit (LRL) to elicit intrinsic beats.

If a predetermined number of intrinsic beats is detected 860 while the pacing mode is modified, SVR characterization is attempted 850. If SVR characterization is successful 865, SVR characterization is complete 870 and the previous pacing regimen is resumed 875. If a sufficient number of intrinsic beats is not detected 860 after the pacing mode is modified, SVR characterization fails 880 and the previous pacing regimen 875 is resumed without SVR characterization. Automatic, active SVR characterization may be terminated prior to completion if predetermined patient conditions are detected. In this event, the previous pacing regimen is resumed. Patient conditions which terminate modified pacing parameters and automatic, active SVR characterization are those previously discussed.

Automatic, active SVR characterization may be attempted if the patient is at rest and if passive SVR characterization has not been successful. A resting state may be indicated, for example, by an appropriate response from a rate responsive subsystem. Further, a resting state may be indicated by a sensed heart rate less than a predetermined rate, such as 110 bpm. In one example, an output signal from the rate responsive subsystem indicates a numerical increase in heart rate above a programmed lower rate limit at which the heart should be pacing in response to the sensor-determined heart rate demand. The patient is determined to be at rest if the numerical increase in heart rate is below a predetermined threshold value, for example 5 bpm. In this situation, the patient's heart rate demand is low and active SVR characterization can proceed. Similarly, if during active SVR characterization, the numerical increase in heart rate indicated by the rate responsive subsystem exceeds the predetermined threshold value, the patient's heart rate demand has increased, and active SVR characterization is terminated, restoring normal pacing functions. In one example, the predetermined threshold value is 5 bpm.

Figure 9:
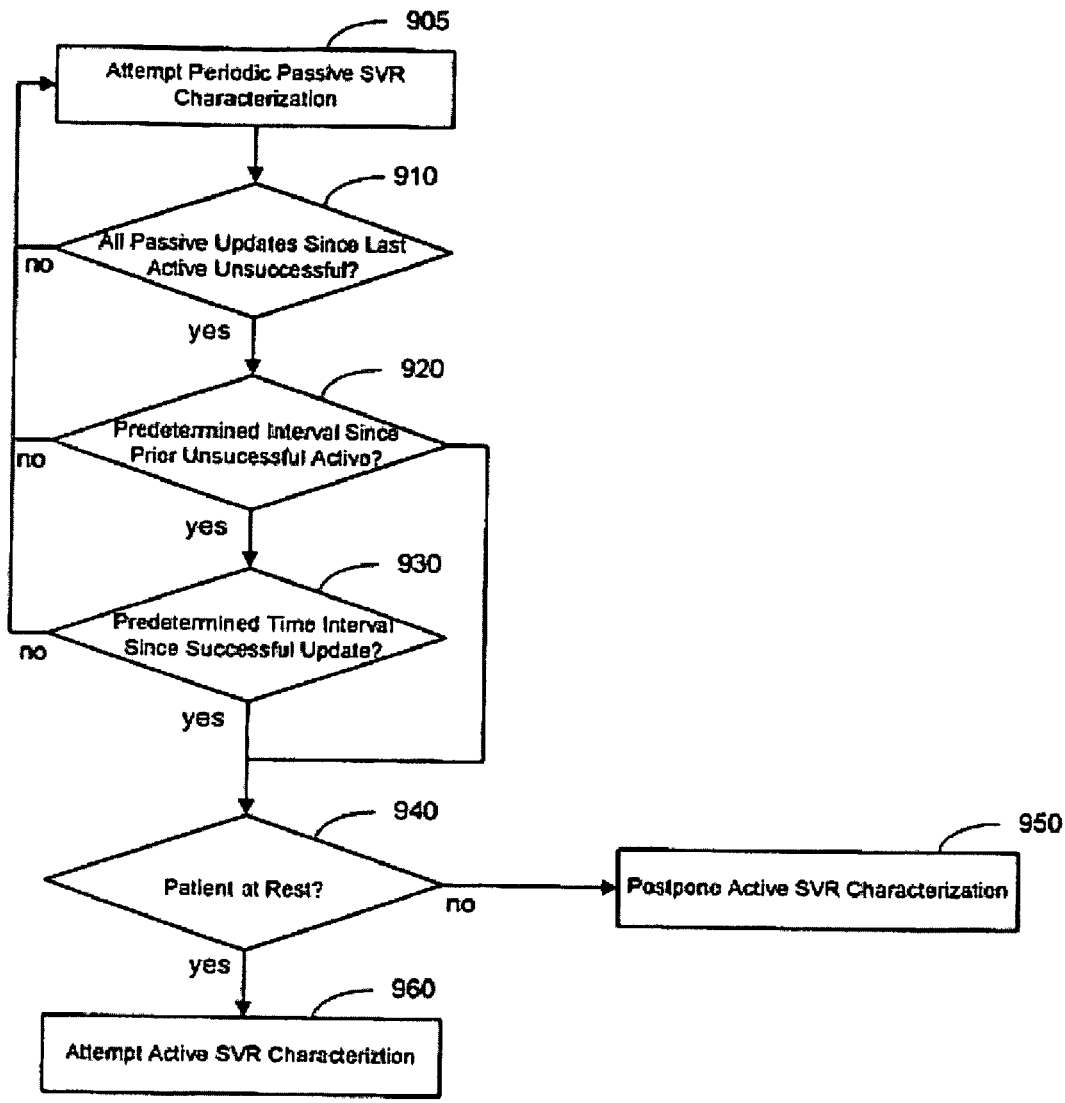
FIG. 9 is a flowchart of a method of determining if an automatic, active SVR characterization may be attempted in accordance with an embodiment of the present invention.

The flowchart of FIG. 9 illustrates the process of determining when active SVR characterization may be attempted. Passive SVR characterization without pacing parameter modification is attempted at regular time intervals 905. In one embodiment, a passive SVR characterization is attempted every two hours, twenty minutes, although any other time interval may be chosen.

If the heart is being constantly or intermittently paced, the passive SVR characterization may be unsuccessful. If all passive SVR characterization attempts since the last active SVR characterization are unsuccessful 910, an active SVR characterization may be automatically attempted. The active SVR characterization attempt may be triggered by various criteria. For example, if a first predetermined interval, for example, 27 hours, or other time interval, has elapsed since the last unsuccessful active attempt 920, an active SVR characterization may be initiated if the patient is at rest 940, as determined by the process previously discussed. A non-24 hour time interval between SVR characterization attempts, such as 27 hours, causes the SVR characterization attempts to occur at different times of day. Attempting SVR characterization in accordance with non-24 hour period intervals increases the likelihood that a suitable time of day will be found for SVR characterization.

Further, if a second predetermined time interval, for example one week, or other designated time interval that is a multiple of 24 hours, has elapsed since the last successful active or passive SVR characterization attempt 930, an active SVR characterization may be initiated if the patient is at rest 940. An interval of one week, or other multiple of a 24 hour period, between SVR characterization attempts is advantageous because it reduces the impact of active SVR characterization on the patient while maintaining an acceptably accurate SVR characterization. Further, an interval which is a multiple of 24 hours causes an SVR characterization attempt to occur at the same time of day (e.g., a time of day associated with successful SVR characterization attempts) without the need for designating an absolute time of day for SVR characterization update. Other criteria may also be used to automatically initiate or inhibit an active SVR characterization attempt.

Prior to beginning an automatic, active SVR characterization, patient conditions are monitored to determine if the patient is at rest 940. If the patient is not in a resting state 940, the automatic, active SVR characterization attempt may be postponed 950 for a predetermined time interval. In one example, an active SVR characterization attempt is postponed for two hours and twenty minutes. If the patient is resting 940, an automatic, active SVR characterization may be initiated 960. Automatic, active SVR characterization is terminated upon detection of physiologic heart rate demand above a predetermined threshold. If SVR characterization is commanded, there may be no requirement to determine if the patient is at rest or to terminate SVR characterization when the patient's physiologic heart rate demand exceeds a particular level. Commanded SVR characterization is assumed to be under the supervision of a physician, therefore, restrictions on patient heart rate demand during SVR characterization may not be necessary.

Figure 10:
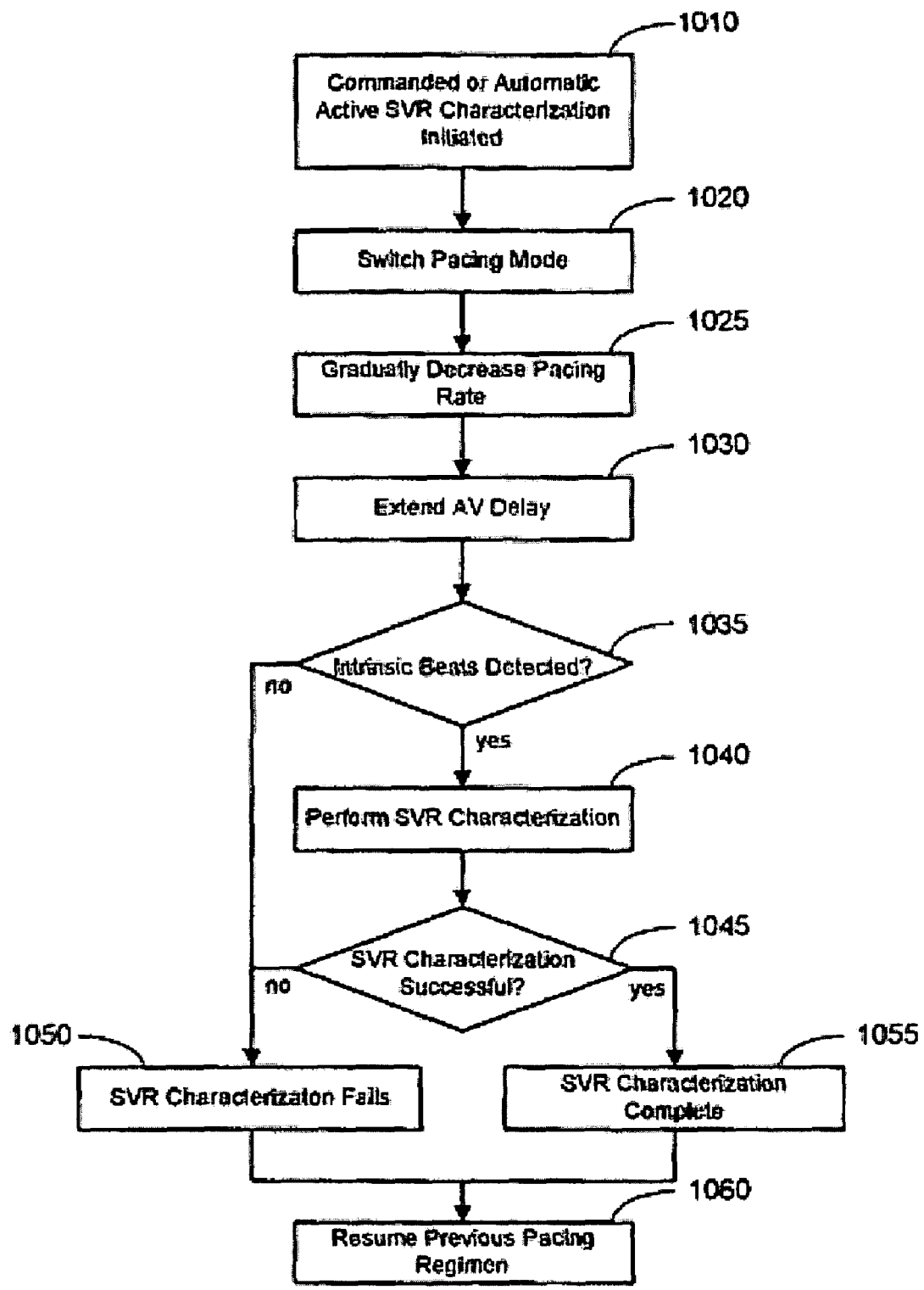
FIG. 10 is a method of performing a commanded or automatic active SVR characterization in accordance with an embodiment of the present invention.

The flowchart of FIG. 10 illustrates the process of active SVR characterization in a dual chamber ICD according to an embodiment of the invention. Following a determination that an active SVR characterization has been automatically initiated or commanded 1010, the pacing mode is switched 1020 to a non-tracking, non-rate responsive mode. Modified pacing modes for automatic and commanded active SVR characterization according to this embodiment are provided in Table 1 below. For example, if the normal pacing mode is DDD(R), tracking and rate responsiveness are suspended, and the pacing mode is modified to DDI during an active SVR characterization attempt. By this method, the normal pacing mode is modified, and any atrial tachycardia response (ATR) pacing modes are ignored during automatic active SVR characterization.

TABLE 1

| Normal pacing | Modified pacing | Programmer warnings in Commanded Mode |
| --- | --- | --- |
| DDD(R) | DDI | |
| DDI(R) | DDI | |
| VDD(R) | VDI | Warning if AAI selected |
| VVI(R) | VVI | Warning if AAI selected |
| AAI(R) | AAI | Warning if VVI selected |
| OOO(R) | OOO (off) | |

In commanded active SVR characterization, the physician may choose a modified pacing mode by transmitting information to the pacemaker through the programmer. The programmer may indicate possible erroneous high risk selections, such as by issuing a warning when switching from ventricular pacing to atrial pacing, for example. In addition, the physician may have control over other pacing mode changes, such as suspending or setting various pacing features, including suspending all dynamic, rate-smoothing, hysteresis, VRR and APP behavior, and setting PVARP to a fixed interval, for example 150 ms.

Following the pacing mode changes indicated above, the pacing rate is gradually slowed to a lower rate limit 1025 and the AV delay is abruptly extended 1030. The pacing rate may be gradually slowed using an ATR algorithm, for example. When operating in commanded mode for SVR characterization, the default lower rate limit achieved by the gradual decrease in pacing rate 1025 may be approximately 45 ppm, for example, or another appropriate rate. The LRL achieved by the gradual decrease in pacing rate 1025 during automatic SVR characterization may be programmable with a default for tracking the normal programmed lower rate limit.

The AV delay may be increased as much as possible while still maintaining safe tachycardia sensing, such as by up to approximately 400 ms. A safe AV delay for tachycardia sensing is the longest AV delay that prevents ventricular undersensing. An extended AV delay, greater that 350 ms, for example, may create a scenario for possible ventricular undersensing because the ventricular blanking interval following atrial pacing is pushed into the tachycardia rate zone. The following rule may be used for determining the safe AV delay: Longest Safe AV Delay=LRI (lower rate interval)–VTI (slowest VT interval)–20 ms (safety window). For example, if the lowest tachycardia zone is 120 bpm, the LRL is 50 bpm, the Longest Safe AV Delay=1200 ms–500 ms–20 ms=680 ms.

Following the pacing rate and AV delay changes, active SVR characterization is attempted. If no intrinsic beats are detected 1035, active SVR characterization fails 1050. However, if the pacing modifications elicit a sufficient number of intrinsic beats, active SVR characterization may be performed. Following successful SVR characterization 1055, or if SVR characterization fails 1050, the normal pacing regimen is reinstated 1060. Original tracking, rate responsiveness, AV delay and other bradycardia related features may be abruptly resumed. If rate smoothing is programmed on, the pacing rate may be gradually restored, otherwise, the pacing rate may be abruptly restored as in the termination of ATR. Following restoration of the pacing rate, the PVARP may be extended for a single beat if PVARP extension is programmed on to prevent ventricular pacing triggered by erroneous sensing of an atrial signal.

During active SVR characterization, various ATR functions may be maintained. For example, ATR up/down counters are maintained during SVR characterization. Further, the ATR duration, begin and end markers are emitted responsive to atrial arrhythmia, and ATR episodes are declared and recorded. Restoring ATR after SVR characterization results in smoothing the pacing rate down to ATR settings if the ATR lower rate limit is slower than the lower rate limit used for SVR characterization. If the ATR lower rate limit is faster than that used during SVR characterization, the increase in pacing rate may be abrupt.

Ventricular paced beats typically trigger a significant increase in the V sense amplifier gain that often results in saturation of the A/D converter by subsequent intrinsic beats. The increased V sense amplifier gain following paced beats is provided to ensure detection of ventricular tachyarrhythmias with low rate channel amplitudes during pacing. It may be advantageous to modify the automatic gain control (AGC) during SVR characterization so that intrinsic beats may be captured without saturation of the A/D converter. The automatic gain control algorithm used to modify the AGC during SVR characterization may delay the increase in gain by a predetermined number of beats. In the event that tachyarrhythmia begins during SVR characterization, this delay may delay therapy for several beats, however, it increases the likelihood of acquiring intrinsic beats for SVR characterization. According to an embodiment of the invention, the rate channel automatic gain control (AGC) algorithm is modified before SVR characterization is attempted so that the ventricular rate channel gain is not modified by a paced beat unless N consecutive pacing pulses have occurred since the last beat, where N=1, 2 or 3.

Figure 11:
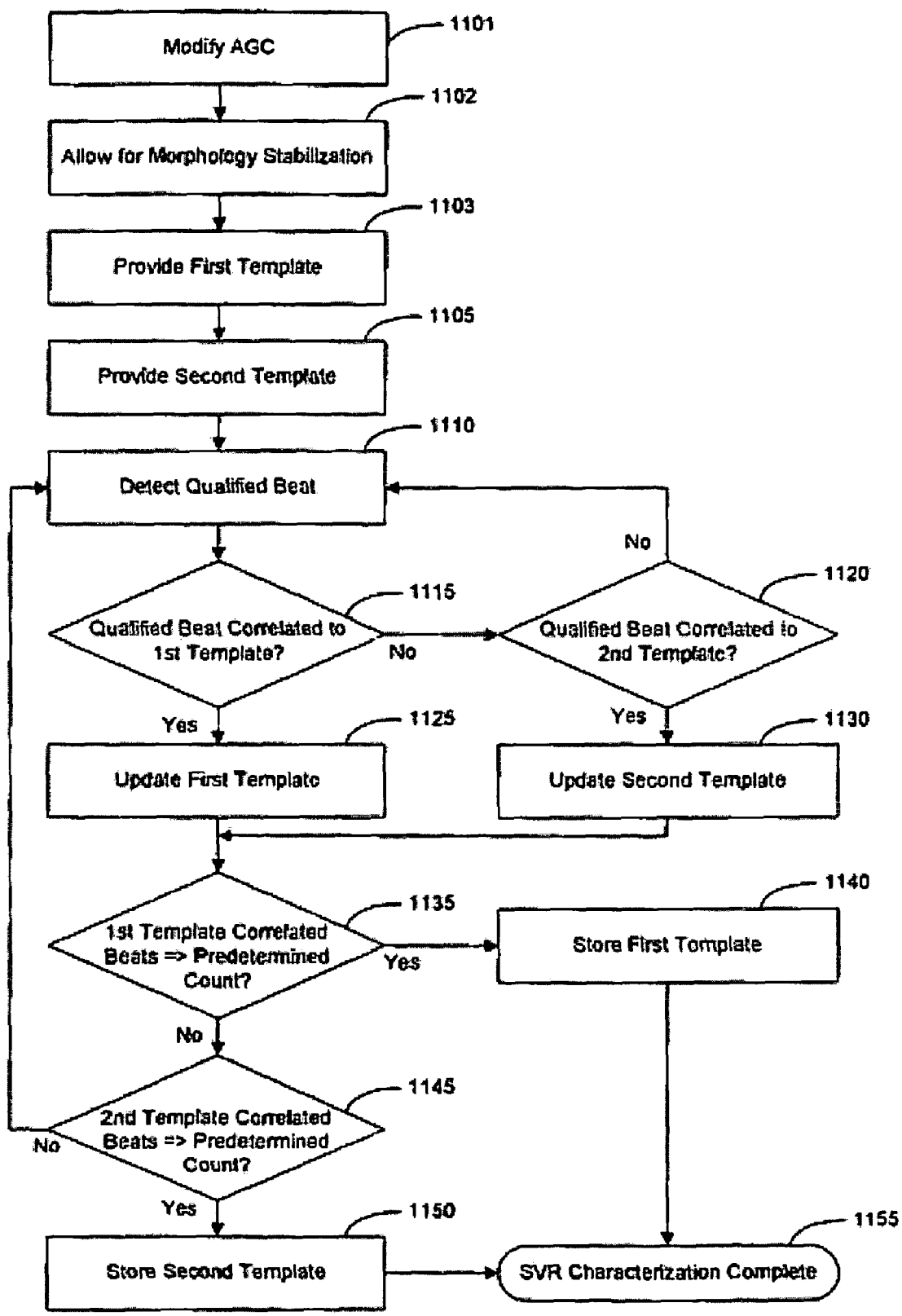
FIG. 11 is a method of SVR characterization using multiple templates in accordance with an embodiment of the invention.

The flowchart of FIG. 11 illustrates a method of using multiple templates to quickly acquire a characterization of a patient's supraventricular rhythm in accordance with the present invention. For the reasons discussed above, prior to commencing SVR characterization, the rate channel AGC is modified 1101. Following detection of intrinsic beats, a predetermined number of beats, for example, four, beats, is required to allow for morphology stabilization before SVR characterization begins. The template generator provides a first template 1103 and a second template 1105. The first template can either be retrieved from memory or can be formed from a first qualified beat.

Three criteria must be met for a beat to be considered a qualified beat suitable for use in SVR characterization. First, the beat and the preceding beat must be intrinsic beats. Second, the preceding V-V interval must be larger than approximately 500 ms and must be regular. A beat is classified as a "regular" beat when the RR interval is larger than 87.5% and less than 150% of the average RR interval. An RR interval is measured as an interval between Vs to Vs, Vs to Vp, Vp to Vs, or Vp to Vp events, where Vs is the ventricular sensed event detection time and Vp is the ventricular pace pulse delivery time. The initial RR average (RRavg) may be calculated as the average of the first four RR intervals. The RRavg may be calculated as a running average. The V-V interval is the interval between successive ventricular beats. Third, the shock channel R-wave amplitude must be larger than approximately 25% of the maximum value of the A/D converter and must not be saturated. Finally, the rate channel R-wave must be larger than approximately 50% of the maximum value of the A/D converter and must not be saturated for more than one consecutive sample. If all three of these conditions are detected, then the beat is considered a qualified beat suitable for characterizing the patient's supraventricular rhythm.

A qualified beat 1110 may be used to update the first template 1125 if the beat is correlated to the first template 1115. If the beat is not correlated to the first template 1115, but is correlated to the second template 1120, the beat is used to update the second template 1130. The following paragraphs describe how correlation of a template and a qualified beat is determined with reference to FIGS. 12-17.

Figure 12:
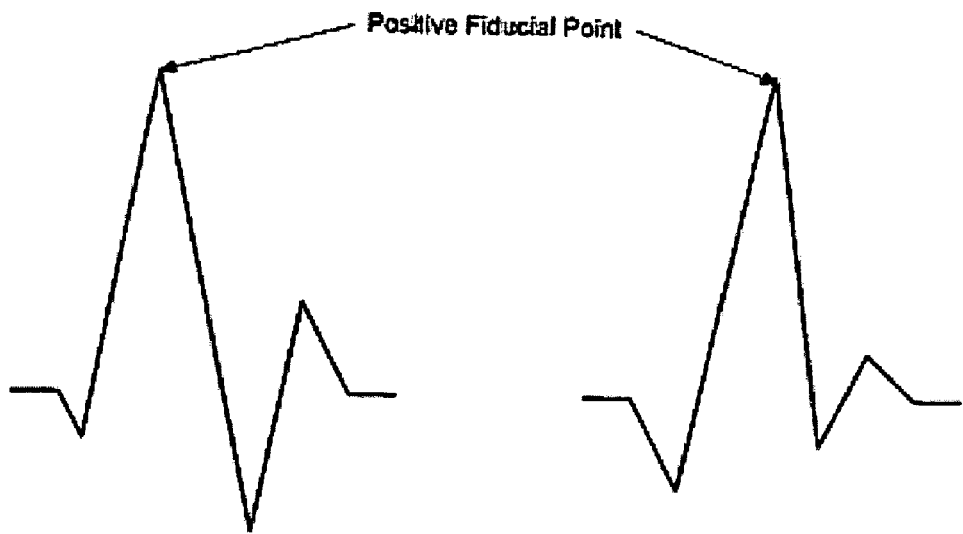
FIGS. 12 and 13 illustrate positive and negative type fiducial points determined from rate channel signals in accordance with an embodiment of the present invention.
Figure 13:
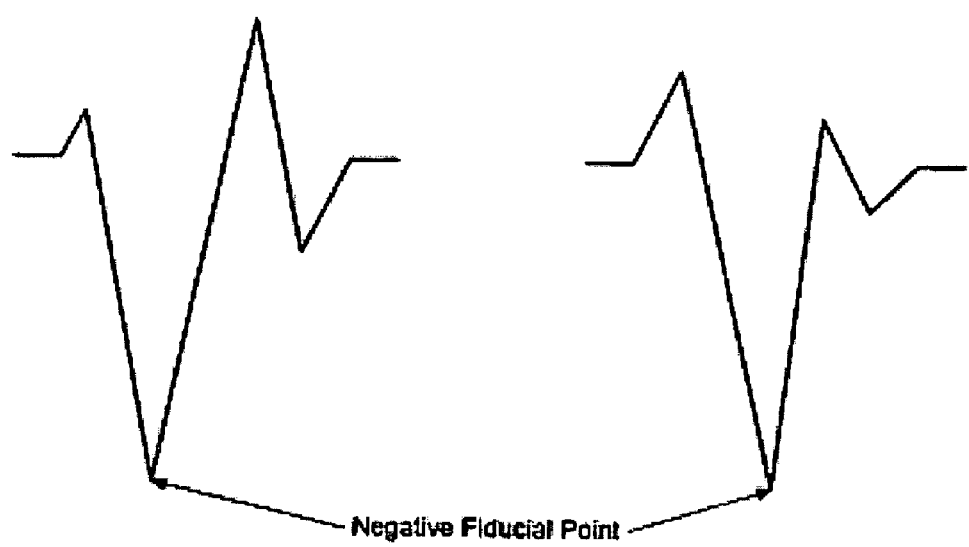

A fiducial point is identified for the template and for the qualified beat. A fiducial point represents a peak value of the rate channel signal. The fiducial point may be either positive, for a positive peak value, or it may be negative, for a negative peak value. Positive and negative fiducial points are illustrated in FIGS. 12 and 13, respectively.

Following determination of the template fiducial point, a plurality of features of the template are identified as illustrated in FIGS. 14-17. In one embodiment of the invention, five features are initially identified for the shock channel template followed by three additional features determined at midpoints between certain ones of the initial five features.

Feature 3 is selected as the absolute maximum peak in a feature window defined by 31 samples centered at the fiducial point. If the positive peak amplitude is equal to the negative peak amplitude, the positive peak is selected as Feature 3.

Feature 2 is found by searching backward from Feature 3 until a point is reached that meets the following conditions: 1) the search is limited to 10 samples. If no point satisfies the following conditions, then the 10th sample becomes Feature 2; 2) the amplitude is less than 25% of the maximum peak; 3) a turning point is found or the slope is flat, and 4) Feature 2 is at least 4 samples away from Feature 3.

By way of example, let Q(I) represent the current sample. A turning point is found if:

$Q(I-1) \geq Q(I)$ and $Q(I) < Q(I+1)$ for a positive Feature 3

$Q(I-1) \leq Q(I)$ and $Q(I) > Q(I+1)$ for a negative Feature 3 [1]

Figure 14:
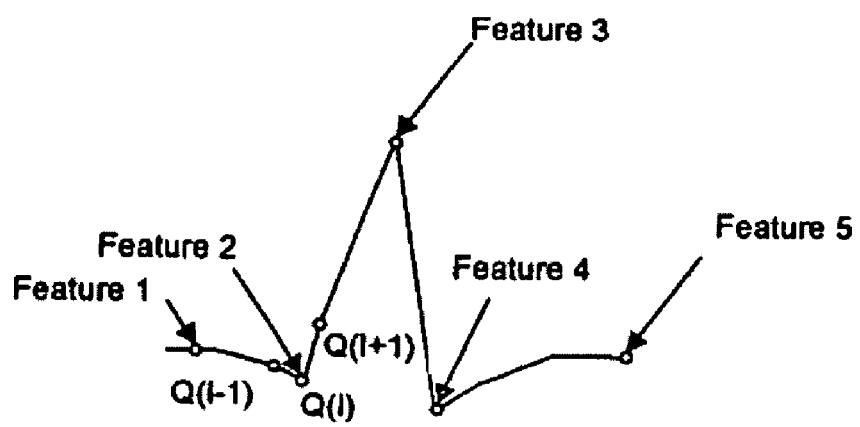
FIGS. 14 and 15 show morphological features, including turning point and flat slope features, respectively, for choosing Feature 2 in accordance with an embodiment of the present invention.

As is shown in FIG. 14, Q(I) is selected as Feature 2. As such, Feature 2 is selected as a turning point.

Figure 15:
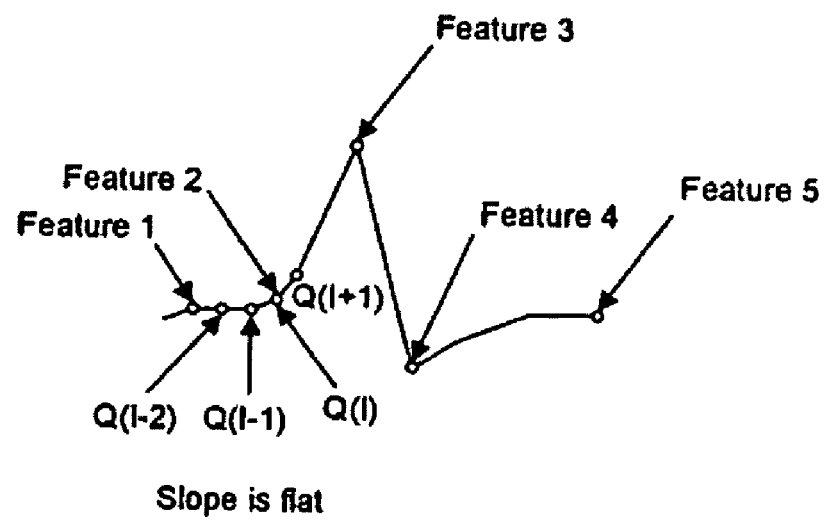

The slope is considered flat, as shown in FIG. 15, if abs(Q(I+1)−Q(I−1))<4 and abs(Q(I+1)−Q(I−2))<4, in the case when the A/D converter maximum value is 128. In the illustrative depiction of FIG. 15, Q(I) is selected as Feature 2. As such, Feature 2 is selected as a flat slope point.

Feature 4 is found by searching forward starting from Feature 3 until a point is reached that meets the following conditions: 1) the search is limited to 16 samples. If no point satisfies the following conditions, then the 16th sample becomes Feature 4; 2) the amplitude is less than 25% of the maximum peak; and 3) a turning point is found or the slope is flat.

By way of example, let Q(I) represent the current sample. A turning point is found if:

$Q(I+1) \geq Q(I)$ and $Q(I) < Q(I-1)$ for a positive Feature 3

$Q(I+1) \leq Q(I)$ and $Q(I) > Q(I-1)$ for a negative Feature 3 [2]

Figure 16:
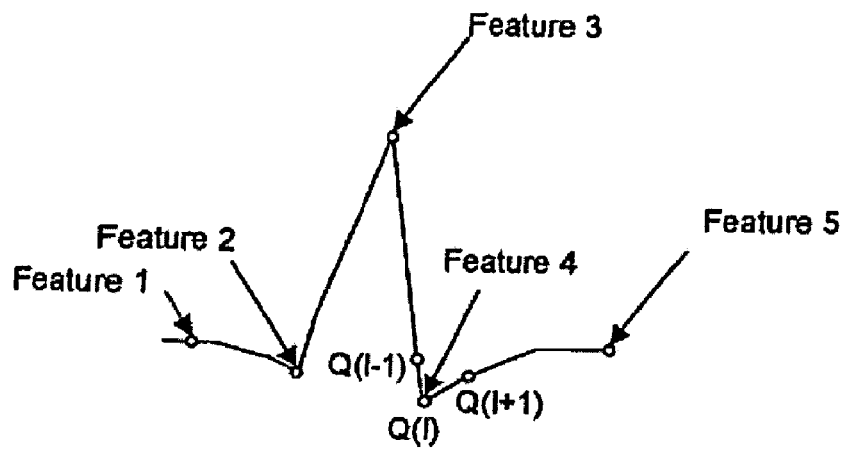
FIGS. 16 and 17 show morphological features, including turning point and flat slope features, respectively, for choosing Feature 4 in accordance with an embodiment of the present invention.

Q(I) is selected as Feature 4, as is shown in FIG. 16.

Figure 17:
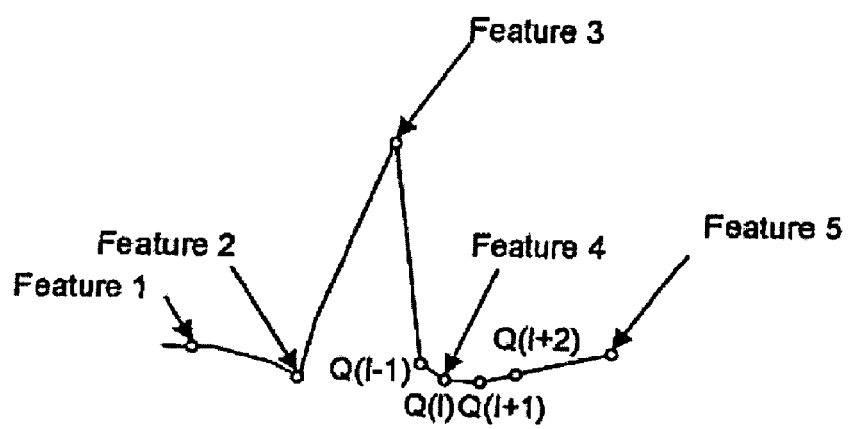

The slope is flat, as shown in FIG. 17, if abs(Q(I−1)−Q(I+1))<4 and abs(Q(I−1)−Q(I+2))<4. In this case, Q(I) is selected as Feature 4.

Feature 1 is selected as the seventeenth sample from the beginning of the detection window. Feature 5 is selected as the last sample of the detection window. Three additional features are selected at the midpoint of Features 1 and 2, the midpoint of Features 2 and 3, and the midpoint of Features 3 and 4, respectively. If a midpoint falls between two sample points, the farthest point in time from Feature 3 is selected. Thus, according to this embodiment, eight feature values (e.g., amplitudes) and their associated locations with respect to the fiducial point and the corresponding fiducial point type are saved for SVR characterization.

The fiducial point of the qualified beat is determined from the rate channel signal of the qualified beat in a manner similar to that set forth above for identifying the template fiducial point. If a positive peak is the template fiducial point, then a positive peak is the fiducial point of the qualified beat. The shock channel waveforms of the template and the qualified beat are aligned using the fiducial points of the template and the qualified beat. The features of the qualified beat are determined at the locations relative to the fiducial point previously determined for the template. The template and the qualified beat are compared by calculating a feature correlation coefficient (FCC). In one particular embodiment, Equation 3, provided below, is used to compute the FCC between the template features and the beat features.

$$FCC = \frac{\left(N \sum_{i=1}^{N} X_i Y_i - \left(\sum_{i=1}^{N} X_i\right)\left(\sum_{i=1}^{N} Y_i\right)\right)^2}{\left(N \sum_{i=1}^{N} X_i^2 - \left(\sum_{i=1}^{N} X_i\right)^2\right)\left(N \sum_{i=1}^{N} Y_i^2 - \left(\sum_{i=1}^{N} Y_i\right)^2\right)} \quad [3]$$

where Xi represents template N features and Yi represents beat N features, and N=8 in this illustrative example. The sign of the numerator term is checked before squaring. If the numerator is negative, the beat is uncorrelated, and the remainder of the computation need not be performed.

If the FCC is greater than or equal to a predetermined value, for example 0.95, then the qualified beat is correlated to the template. If the FCC is less than the predetermined value, then the qualified beat is uncorrelated to the template.

Returning now to FIG. 11, if a beat is correlated to the first template 1115, it is used to update the first template 1125. If the beat is uncorrelated to the first template 1115, but is correlated to the second template 1120, the beat is used to update the second template 1130. A template is updated by point-by-point addition of the template waveform and the shock channel waveform of the qualified beat after alignment of the waveforms using previously determined fiducial points.

The templates continue to be updated in this manner until either the first or the second template is updated with a predetermined number of beats. If the first template is updated with a predetermined number of beats 1135, the first template is stored 1140 as the characterization of the patient's supraventricular rhythm and SVR characterization is complete 1155. If the first template is not correlated to the predetermined number of beats 1135 but the second template has been correlated to the predetermined number of beats 1145, the second template is stored 1150 as a representative of the patient's supraventricular rhythm and SVR characterization is complete 1155.

The process discussed above for SVR characterization is but one example of various methods that may be used to characterize a patient's supraventricular rhythm.

SVR characterization in accordance with the principles of the present invention provides for several advantages. For example, SVR characterization in accordance with the present invention provides a method for characterizing a patient's normal sinus rhythm when the heart is being constantly or intermittently paced. In addition, the method of SVR characterization of the present invention requires only beat-by-beat analysis and is efficient in memory usage making it well-suited for use in implantable devices, such as in implantable cardioverter/defibrillator devices. Further, SVR characterization by this method requires a relatively small number of beats as compared to other methods, making the SVR characterization method of the present invention particularly useful when the patient's heart is being intermittently or constantly paced.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of characterizing a patient's supraventricular rhythm while the heart is being paced, comprising:
pacing the patient's heart;
modifying at least one pacing parameter, comprising at least one of modifying an AV delay, modifying a pacing rate, modifying a pacing interval, suspending at least one of pacemaker functions, and modifying a pacemaker mode at least by changing the pacemaker mode from a tracking mode to a non-tracking mode; and
characterizing the patient's supraventricular rhythm during a time in which the at least one pacing parameter is modified.

2. The method of claim 1, further comprising resuming a pacing regimen following characterization of the patient's supraventricular rhythm or if the characterization of the patient's supraventricular rhythm is unsuccessful.

3. The method of claim 1, wherein the characterization of the patient's supraventricular rhythm is performed automatically or upon command.

4. The method of claim 1, wherein the patient's supraventricular rhythm is characterized at a time when the patient's sensed physiologic heart rate demand indicates the patient is at rest.

5. The method of claim 1, wherein modifying the AV delay comprises at least one of:
lengthening the AV delay incrementally by a predetermined interval each beat until an AV delay limit is reached during dual chamber pacing; and
lengthening the AV delay by a predetermined delay, and the predetermined delay is a longest safe AV delay for tachycardia sensing.

6. The method of claim 1, wherein modifying the pacemaker mode comprises at least changing the pacemaker mode from a tracking, rate responsive mode to a non-tracking, non-rate responsive mode.

7. The method of claim 1, wherein modifying the pacemaker mode comprises modifying the pacemaker mode if a predetermined number intrinsic beats is not detected after increasing the AV delay until an AV delay limit is reached.

8. The method of claim 1, wherein modifying the pacing rate includes decreasing the pacing rate to a lower rate limit.

9. The method of claim 1, wherein modifying the at least one pacing parameter comprises at least one of:
suspending left side pacing when both ventricles of the patient's heart are being paced prior to modification; and
increasing a V-V interval by a predetermined time interval each beat until a lower rate limit is reached during single chamber pacing.

10. The method of claim 1, wherein suspending at least one of pacemaker functions includes suspending at least one of rate smoothing up, rate smoothing down, dynamic AV delay, dynamic postventricular atrial refractory period, AV search interval, rate hysteresis offset, sensed AV delay offset, postventricular atrial refractory period after premature ventricular complex, dynamic ventricular refractory period, and ventricular rate regularization.

11. An implantable system for characterizing a patient's supraventricular rhythm while the patient's heart is being paced, comprising:
a lead system comprising at least one electrode and configured to electrically couple to the patient's heart;
a detector system coupled to the lead system; and
a control system coupled to the detector system and configured to control pacing of the patient's heart and to control at least one of modifying an AV delay, modifying a pacing rate, modifying a pacing interval, suspending at least one of pacemaker functions, and modifying a pacemaker mode at least by changing the pacemaker mode from a tracking mode to a non-tracking mode, the control system configured to characterize the patient's supraventricular rhythm during a time in which the at least one pacing parameter is modified.

12. The system of claim 11, comprising a rate responsive subsystem coupled to the control system for providing an output indicating a patient's physiologic heart rate demand, wherein the control system is configured to characterize the patient's supraventricular rhythm at a time when the patient's sensed physiologic heart rate demand indicates the patient is at rest.

13. The system of claim 11, comprising a rate responsive subsystem coupled to the control system for providing an output indicating a patient's physiologic heart rate demand, wherein the control system is configured to modify the pacemaker mode by changing the pacemaker mode from a tracking, rate responsive mode to a non-tracking, non-rate responsive mode based at least on signals received from the rate responsive subsystem.

14. The system of claim 11, wherein the control system is configured to modify the AV delay by lengthening the AV delay incrementally by a predetermined interval each beat until an AV delay limit is reached during dual chamber pacing.

15. The system of claim 11, wherein the control system is configured to modify the AV delay by lengthening the AV delay by a predetermined delay, and the predetermined delay is a longest safe AV delay for tachycardia sensing.

16. The system of claim 11, wherein the control system is configured to modify the pacemaker mode if a predetermined number of intrinsic beats is not detected after increasing the AV delay until an AV delay limit is reached.

17. The system of claim 11, wherein modifying the pacing rate includes decreasing the pacing rate to a lower rate limit.

18. The system of claim 11, wherein the control system is configured to modify the at least one pacing parameter by at least one of suspending left side pacing when both ventricles of the patient's heart are being paced prior to modification, and increasing a V-V interval by a predetermined time interval each beat until a lower rate limit is reached during single chamber pacing.

19. The system of claim 11, wherein the control system is configured to suspend at least one of rate smoothing up, rate smoothing down, dynamic AV delay, dynamic postventricular atrial refractory period, AV search interval, rate hysteresis offset, sensed AV delay offset, postventricular atrial refractory period after premature ventricular complex, dynamic ventricular refractory period, and ventricular rate regularization.

20. A system for characterizing a patient's supraventricular rhythm while the heart is being paced, comprising:
 a pulse generator configured to pace the patient's heart;
 means for modifying at least one pacing parameter, comprising at least one of modifying an AV delay, modifying a pacing rate, modifying a pacing interval, suspending at least one of pacemaker functions, and modifying a pacemaker mode at least by changing the pacemaker mode from a tracking mode to a non-tracking mode; and
 means for characterizing the patient's supraventricular rhythm during a time in which the at least one pacing parameter is modified.

\* \* \* \* \*